US012665050B2

(12) United States Patent
Barbacioru et al.

(10) Patent No.: US 12,665,050 B2
(45) Date of Patent: ***Jun. 23, 2026

(54) COMPUTATIONAL MODELING OF LOSS OF FUNCTION BASED ON ALLELIC FREQUENCY

(71) Applicant: GUARDANT HEALTH, INC., Redwood City, CA (US)

(72) Inventors: Catalin Barbacioru, Redwood City, CA (US); Marcin Sikora, Redwood City, CA (US); Darya Chudova, San Jose, CA (US)

(73) Assignee: GUARDANT HEALTH, INC., Palo Alto, CA (US)

( * ) Notice: Subject to any disclaimer, the term of this patent is extended or adjusted under 35 U.S.C. 154(b) by 618 days.

This patent is subject to a terminal disclaimer.

(21) Appl. No.: 16/803,680

(22) Filed: Feb. 27, 2020

(65) Prior Publication Data

US 2020/0273538 A1     Aug. 27, 2020

Related U.S. Application Data

(60) Provisional application No. 62/823,585, filed on Mar. 25, 2019, provisional application No. 62/811,159, filed on Feb. 27, 2019.

(51) Int. Cl.
| | |
|---|---|
| *G16B 20/20* | (2019.01) |
| *C12Q 1/6809* | (2018.01) |
| *G16H 50/20* | (2018.01) |

(52) U.S. Cl.
CPC ............. *G16B 20/20* (2019.02); *G16H 50/20* (2018.01); *C12Q 1/6809* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,582,908 B2 | 6/2003 | Fodor et al. | |
| 7,537,898 B2 | 5/2009 | Bost et al. | |
| (Continued) | | | |

FOREIGN PATENT DOCUMENTS

| | | | | |
|---|---|---|---|---|
| WO | WO-2014183078 A1 | * | 11/2014 | ............. G16B 20/00 |
| WO | 2018144782 A1 | | 8/2018 | |
| WO | WO-2019020652 A1 | * | 1/2019 | ........... C12Q 1/6827 |

OTHER PUBLICATIONS

Chen et al. PSSV: a novel pattern-based probabilistic approach for somatic structural variation identification. Bioinformatics, 33(2), 2017, 177-183 (Year: 2017).*

(Continued)

*Primary Examiner* — Karlheinz R. Skowronek
*Assistant Examiner* — Mary C Leverett
(74) *Attorney, Agent, or Firm* — Timothy A. Hott

(57) ABSTRACT

The disclosure relates to computer technology for precision diagnosis of various states of genetic material such as a gene sequenced from cell-free DNA in a sample. The state may include a somatic homozygous deletion, a somatic heterozygous deletion, a copy number variation, or other states. A computer system may generate competing probabilistic models that each output a probability that the genetic material is in a certain state. Each model may be trained on a training sample set to output a probability that the genetic material is in a respective state. In some embodiments, the computer system may use various probabilistic distributions to generate the models. For example, the computer system may use a beta-binomial distribution, a binomial distribu- (Continued)

tion, a normal (also referred to as "Gaussian") distribution, or other type of probabilistic modeling techniques.

19 Claims, 22 Drawing Sheets

(56) References Cited

U.S. PATENT DOCUMENTS

| | | | |
|---|---|---|---|
| 9,598,731 B2 | 3/2017 | Talasaz | |
| 9,902,992 B2 | 2/2018 | Talasaz et al. | |
| 2001/0053519 A1 | 12/2001 | Fodor et al. | |
| 2003/0152490 A1 | 8/2003 | Trulson et al. | |
| 2011/0160078 A1 | 6/2011 | Fodor et al. | |
| 2017/0342477 A1* | 11/2017 | Jensen | C12Q 1/6858 |
| 2018/0218113 A1 | 8/2018 | Sun et al. | |
| 2018/0373832 A1 | 12/2018 | Sakarya et al. | |

OTHER PUBLICATIONS

Dawson et al. Analysis of Circulating Tumor DNA to Monitor Metastatic Breast Cancer. N Engl J Med 2013;368:1199-209. (Year: 2013).*

Kalatskaya et al. ISOWN: accurate somatic mutation identification in the absence of normal tissue controls. Genome Medicine (2017) 9:59 (Year: 2017).*

Smith et al. SomVarIUS: somatic variant identification from unpaired tissue samples. Bioinformatics, 32(6), 2016, 808-813 (Year: 2016).*

Peck R. Olsen C. & Devore J. L. (2008). Introduction to statistics and data analysis (3rd ed.) Chapter 7.4. Thomson Brooks/Cole. (Year: 2008).*

Barbacioru, C. et al. "Abstract 435: Cell-free circulating tumor DNA (ctDNA) detects somatic copy number loss in homologous recombination repair genes" Clinical Research (Excluding Clinical Trials) (2019) p. 435, XP055701312.

Christoforides, A. et al. "Identification of somatic mutations in cancer through Bayesian-based analysis of sequenced genome pairs" BMC Genomics, Biomed Central (2013) 14(1):302.

Harismendy, O. et al. "Evaluation of ultra-deep targeted sequencing for personalized breast cancer care" Breast Cancer Res (2013) 15(6):R115.

International search report and written opinion dated Aug. 5, 2020 for PCT/US2020/020174.

Jonsson, P. et al. "Tumour lineage shapes BRCA-mediated phenotypes Nature" 571(7766):576-579.

Kim, S. et al. "Strelka2: fast and accurate calling of germline and somatic variants" Nature Methods (2018) 15(8):591-594.

Nance, T. et al. "Abstract 4272: A novel approach to differentiation of somatic vs. germline variants in liquid biopsies using a betabinomial model" Proceedings: AACR Annual Meeting (2018) XP055701333, DOI:10.1158/1538-7445.

Robinson, D. et al. "Integrative clinical genomics of advanced prostate cancer" Cell (2015) 161:1215-1228.

Non-final Office Action for U.S. Appl. No. 18/569,130 dated Dec. 5, 2023.

Chinese Office Action for CN Application No. 2020800319400 dated Jul. 11, 2024.

European Office Action for EP Application No. 20714778.6, dated Jul. 24, 2024.

Office Action for U.S. Appl. No. 18/469,130, dated Mar. 4, 2024.

Adalsteinsson, V.A. et al. "Scalable whole-exome sequencing of cell-free DNA reveals high concordance with metastatic tumors." Nature communications 8.1 (2017): 1324.

Faraoni, I. et al. "Role of BRCA mutations in cancer treatment with poly (ADP-ribose) polymerase (PARP) inhibitors." Cancers 10.12 (2018): 487.

Office Action in U.S. Appl. No. 18/347,986, dated Oct. 2, 2024.

Chen, G.K. et al. "Precise inference of copy number alterations in tumor samples from SNP arrays" Bioinformatics (2013) 29(23):2964-2970.

Ha, G. et al. "Integrative analysis of genome-wide loss of heterozygosity and monoallelic expression at nucleotide resolution reveals disrupted pathways in triple-negative breast cancer" Genome Res (2012) 22:1995-2007.

* cited by examiner

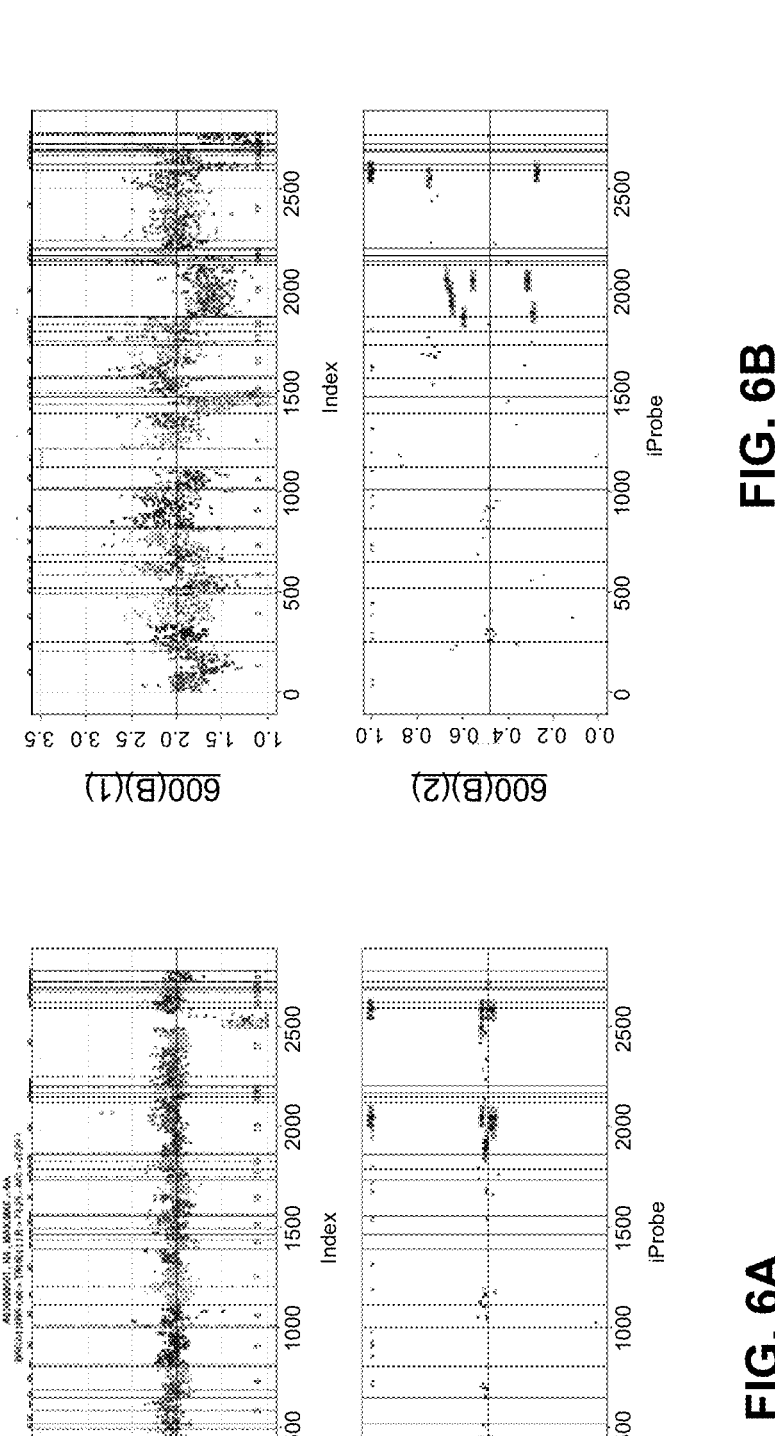
Example of BRCA1 homozygous deletion
Example of BRCA2 heterozygous deletion
FIG. 6A
FIG. 6B

MAF across TND samples

Het prevalence across TND samples

COMPUTATIONAL MODELING OF LOSS OF FUNCTION BASED ON ALLELIC FREQUENCY

CROSS-REFERENCE TO RELATED APPLICATIONS

This application claims the benefit of priority of U.S. Provisional Application No. 62/811,159, filed Feb. 27, 2019, and U.S. Provisional Application No. 62/823,585, filed on Mar. 25, 2019, which are incorporated by reference herein for all purposes.

BACKGROUND

A tumor is an abnormal growth of cells. Fragmented DNA is often released into bodily fluid when cells, such as tumor cells, die. Thus, some of the cell-free DNA in body fluids is tumor DNA. A tumor can be benign or malignant. A malignant tumor is often referred to as a cancer.

Cancer is a major cause of disease worldwide. Each year, tens of millions of people are diagnosed with cancer around the world, and more than half eventually die from it. In many countries, cancer ranks as the second most common cause of death following cardiovascular diseases. Early detection is associated with improved outcomes for many cancers.

Cancer is caused by the accumulation of mutations and/or epigenetic variations within an individual's normal cells, at least some of which result in improperly regulated cell division. Such mutations, or states of genetic material, commonly include copy number variations (CNVs), copy number aberrations (CNA), single nucleotide variations (SNVs), gene fusions and indels, and epigenetic variations include modifications to the 5th atom of the 6-atom ring of cytosine and association of DNA with chromatin and transcription factors.

In a particular example, loss of heterozygosity (LOH) and biallellic copy number loss of homologous recombination repairs (HRR) genes (BRCA1/2) are associated with loss of function of tumor suppression, leading to cancer. In many instances, the particular state of a gene of interest may inform a type of treatment. For example, one state of the gene may be responsive to a set of drugs while another state of the gene may not. Thus, it is increasingly important to be able to not only diagnose cancers and other diseases, but also to characterize the root cause of disease.

Cancers are often detected by biopsies of tumors followed by analysis of cells, markers or DNA extracted from cells. Research is underway to detect cancer based on an analysis of bodily fluids. If successful, these tests have the advantage that they are non-invasive and can be performed without identifying suspected cancer cells through biopsy. However, successfully completing these types of tests are complicated by the fact that the amount of nucleic acids in body fluids is very low. Furthermore, the amount of detectable tumor-related cell-free nucleic acids in body fluids may further make analysis and detection of cancer in cell-free DNA difficult. In other words, tumor DNA in bodily fluids may be contaminated with normal DNA, making computational analysis and detection of the specific cause of tumors in samples of cell-free DNA difficult.

SUMMARY

The disclosure relates to computer technology that provides precision diagnosis of various states of genetic material such as a gene sequenced from cell-free DNA in a sample. The state may include a mutational state of the gene such as, without limitation, a somatic homozygous deletion, a somatic heterozygous deletion, a copy number variation ("CNV") (including a specific copy number wildtype, amplification, or loss), and/or other states. The precision diagnostics may be based on one or more probabilistic models of the states. For example, a computer system may generate competing models that each output probabilities that genetic material is in a certain state.

Each model may be trained on a training sample set to output a probability that the genetic material is in a respective state. For example, a first model may relate to and output a first probability that the genetic material includes a somatic homozygous deletion of an allele of a particular gene. A second model may relate to and output a second probability that the genetic material includes a somatic heterozygous deletion of an allele of a particular gene. Other models may relate to and output a probability of other types of states, such as CNV of genetic material. The computer system may compare the outputs of each competing model to determine which one is more likely. For example, the computer system may use a log likelihood ratio of the competing first and second probabilities to determine whether the genetic material includes a somatic homozygous deletion or somatic heterozygous deletion.

In some embodiments, the computer system may use various probabilistic distributions to generate the models. For example, the computer system may use a beta-binomial distribution, a binomial distribution, a normal (also referred to as "Gaussian") distribution, and/or other type of probabilistic modeling techniques. The computer system may model the states (such as allelic counts that support a specific state) based on training datasets to set baseline expectations of non-normal, or tumor, states. For example, the computer system may identify germline single nucleotide polymorphism (SNP) positions observed in "normal" or non-tumor samples, for example samples in which no somatic variants are observed. These samples will also be referred to as tumor not detected (TND) samples.

Because the TND samples are normal, the computer system may assume that the germline SNP positions do not contribute to a non-normal state. As such, the computer system may leverage these SNP sites to serve as a reference expectation for modeling allelic counts for probabilistic determinations of the state. For instance, deviation from the observed nucleotide calls at each SNP position may indicate a probability that such deviation contributes to a particular state, such as a tumor or other non-normal state. The computer system may accordingly train the models based on expectations derived from computations on data from the germline SNPs of the TND samples. Such computed data may include, for each SNP site: a prevalence of heterozygosity, a standard deviation of MAF, a genotype, a germline prevalence (priors), and/or other data that may inform analysis of a sample of an individual.

With the expectations computed, the computer system may model the states based on sequence reads of a sample of an individual being tested that align to a region of interest, such as a region upstream, downstream, and including a gene of interest. In some embodiments, sequence reads of molecules generated from the sample of the individual may be aligned against the reference genome to identify an allele (mutant or wildtype) that an underlying molecule supports. Based on the alignment of sequence reads generated from the sample of the individual, the computer system may identify a number of molecules that support an alternate allele and calculate a total number of molecules. The computer system may model these and/or other data from the sample of the individual with the expectation data computed from each of the germline SNPs in the region of interest. In some examples, the sequencing may be based on targeted sequencing of plasma cell-free DNA (cfDNA).

In one aspect, the disclosure relates to a computer system improved to distinguish between a somatic homozygous deletion and a somatic heterozygous deletion of a gene in a sample that does not exhibit germline deletion of the gene. The computer system may include a processor programmed to: generate, via a first probabilistic distribution, a first model of allelic counts based on one or more germline single nucleotide polymorphism (SNP) positions associated with the gene, the first model representing the somatic homozygous deletion. The processor may further generate, via a second probabilistic distribution, a second model of allelic counts in the sample based on the one or more germline SNP positions, the second model representing the somatic heterozygous deletion. The processor may compare a first output of the first model and a second output of the second model. The processor may generate a prediction that the somatic homozygous deletion for the gene exists in the sample based on the comparison.

In some embodiments, the first model may represent a first probability that the sample includes the somatic homozygous deletion and the second model represents a second probability that the sample includes the somatic heterozygous deletion.

In some embodiments, the first probabilistic distribution is a same type of probabilistic distribution as the second probabilistic distribution.

In some embodiments, to generate the first model, the processor is programmed to determine one or more parameters for input to the first probabilistic distribution.

In some embodiments, the first probabilistic distribution includes a beta-binomial distribution, a binomial distribution, or a normal distribution.

In some embodiments to generate the first model of allelic counts, the processor may further determine, for input to the first probabilistic distribution, a prevalence of heterozygosity of the one or more germline SNPs in a training set of samples.

In some embodiments, wherein the training set of samples may include a plurality of samples in which tumor is not detected (TND).

In some embodiments, to generate the first model of allelic counts, the processor may further determine, for input to the first probabilistic distribution, a standard deviation of a minor allele frequency (MAF) associated with each of the one or more germline SNPs in the training set of samples.

In some embodiments, to generate the first model, the processor may further determine, for input to the first probabilistic distribution, a number of molecules in the sample that supports a mutant allele.

In some embodiments, to generate the first model, the processor may further determine, for input to the first probabilistic distribution, a total number of molecules in the sample.

In some embodiments, to generate the first model, the processor may further calculate a first likelihood of the allelic counts of the one or more germline SNP positions in the sample assuming somatic homozygous deletion based on sequence read coverage associated with the somatic homozygous deletion.

In some embodiments, to generate the second model, the processor may further calculate a second likelihood of the allelic counts of the one or more germline SNP positions in the sample assuming somatic heterozygous deletion based on sequence read coverage associated with the somatic heterozygous deletion.

In some embodiment, to generate the second model, the processor may further determine, for input to the second probabilistic distribution for the second model, a mean of tumor fraction estimated from the sample.

In some embodiments, the tumor fraction may be estimated based on sequence coverage information.

In some embodiments, to generate the second model, the processor may further determine, for input to the second probabilistic distribution for the second model, a standard deviation of tumor fraction estimated from the sample.

In some embodiments, the processor may further access a plurality of samples, identify a set of samples from among the plurality of samples that include a germline deletion, filter out the set of samples from the plurality of samples, and identify, from among the filtered plurality of samples, a presence of the somatic homozygous deletion or the somatic heterozygous deletion.

In some embodiments, the first output may include a first probability of a presence of the somatic homozygous deletion and the second output may include a second probability of a presence of the somatic heterozygous deletion.

In some embodiments, to compare the first output of the first model and the second output of the second model, the processor may further execute a log likelihood function based on the first output and the second output.

In some embodiments, the gene may include BRCA1, BRCA2, or ATM.

In another aspect, the disclosure relates to a system. The system may include a processor programmed to generate a first probability that a gene in a sample includes a somatic homozygous deletion, generate a second probability that the gene in the sample includes a somatic heterozygous deletion, compare the first probability and the second probability, and generate a prediction of whether the sample includes the somatic homozygous deletion or the somatic heterozygous deletion.

In another aspect, the disclosure relates to a system. The may include a processor programmed to generate a first probability that genetic material in a sample includes a first state, generate a second probability that the genetic material in the sample includes a second state, compare the first probability and the second probability, and generate a prediction of whether the sample includes the first state or the second state.

In some embodiments, the first state comprises a somatic homozygous deletion and the second state comprises a somatic heterozygous deletion.

In some embodiments, the first state may include a first copy number variant (CNV) and the second state may include a second CNV different from the first CNV.

In some embodiments, the first CNV and/or the second CNV may be associated with a deleterious state.

In some embodiments, to generate the first probability, the processor may further access one or more germline single nucleotide polymorphism (SNP) positions associated with the gene, and determine a standard deviation of a minor allele frequency (MAF) associated with each of the one or more germline SNPs in a training set of samples.

In some embodiments, to generate the first probability, the processor may further determine, for input to the probabilistic distribution, a standard deviation of a minor allele frequency (MAF) associated with each of the one or more germline SNPs in the training set of samples.

In another aspect, the disclosure relates to a method implemented by a processor. The method may include generating, by the processor, via a first probabilistic distribution, a first model of allelic counts based on one or more germline single nucleotide polymorphism (SNP) positions associated with the gene, the first model representing the somatic homozygous deletion. The method may further include generating, by the processor, via a second probabilistic distribution, a second model of allelic counts in the sample based on the one or more germline SNP positions, the second model representing the somatic heterozygous deletion. the method may include comparing, by the processor, a first output of the first model and a second output of the second model. The method may further include generating, by the processor, a prediction that the somatic homozygous deletion for the gene exists in the sample based on the comparison.

In another aspect, the disclosure relates to another method implemented by a processor. The may include generating, by the processor, a first probability that the gene in the sample includes a somatic homozygous deletion. The method may further include generating, by the processor, a second probability that the gene in the sample includes a somatic heterozygous deletion. The method may further include comparing, by the processor, the first probability and the second probability. The method may further include generating, by the processor, a prediction of whether the sample includes the somatic homozygous deletion or the somatic heterozygous deletion.

In another aspect, the disclosure relates to another method implemented by a processor.

The method may include generating, by the processor, a first probability that genetic material in the sample includes a first state. The method may further include generating, by the processor, a second probability that genetic material in the sample includes a second state. The method may further include comparing, by the processor, the first probability and the second probability. The method may further include generating, by the processor, a prediction of whether the sample includes the first state or the second state.

In another aspect, the disclosure relates to a method for administering to a subject determined to have a somatic homozygous deletion based on the disclosure herein, a therapeutic intervention effective to treat a cancer associated with the somatic homozygous deletion.

In some embodiments, the therapeutic intervention may include a poly ADP ribose polymerase (PARP) inhibitor. Examples of a PARP inhibitor include OLAPARIB, TALA-ZOPARIB, RUCAPARIB, NIRAPARIB (trade name ZEJULA), among others.

In some embodiments, the therapeutic intervention may include a base excision repair (BER) inhibitor. For example, OLAPARIB may inhibit BER.

In another aspect, the disclosure relates to a method for administering to a subject determined to have a particular state of genetic material based on the disclosure herein, a therapeutic intervention effective to treat a disease associated with the state of the genetic material.

In another aspect, the disclosure relates to a method for administering to a subject determined not to have a somatic homozygous deletion based on the disclosure herein, a therapeutic intervention to exclude a PARP inhibitor.

In some embodiments of each and every aspect of the disclosure, the results of the systems and/or methods disclosed herein are used as an input to generate a report. The report may be in a paper or electronic format. For example, information on, and/or information derived from, the deletion or other status of a gene and/or genetic material, as determined by the methods or systems disclosed herein, can be displayed in such a report. The methods or systems disclosed herein may further comprise communicating the report to a third party, such as the subject from whom the sample derived or a health care practitioner.

The various operations of the methods disclosed herein, or the operations carried out by the systems disclosed herein, may be carried out at the same time or different times, and/or in the same geographical location or different geographical locations, e.g. countries. The various steps of the methods disclosed herein can be performed by the same person or different people.

BRIEF DESCRIPTION OF THE FIGURES

FIG. 6A illustrates an example plot of a BRCA1 homozygous deletion, according to an embodiment of the disclosure.

FIG. 6B illustrates an example plot of a BRCA2 heterozygous deletion, according to an embodiment of the disclosure.

DEFINITIONS

Figure 1:
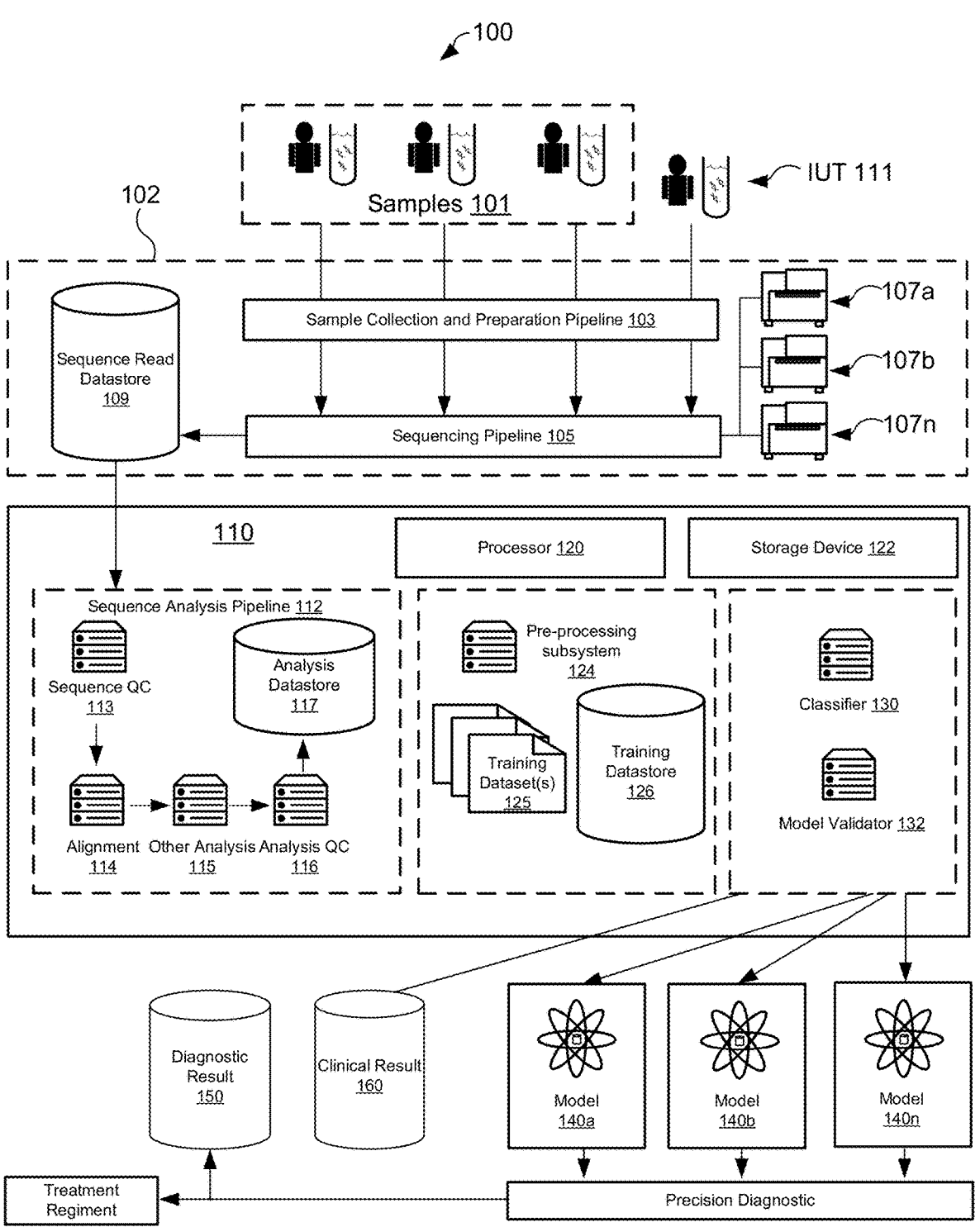
FIG. 1 illustrates an example of a system for training models to predict a state of genetic materials based on probabilities of each state, according to an embodiment of the disclosure.

A subject refers to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease or a predisposition to the disease, or an individual that is in need of therapy or suspected of needing therapy.

A genetic variant refers to an alteration, variant or polymorphism in a nucleic acid sample or genome of a subject. Such alteration, variant or polymorphism can be with respect to a reference genome, which may be a reference genome of the species (e.g., for human, hG19 or hG38), the subject or other individual. Variations include one or more single nucleotide variations (SNVs), insertions, deletions, repeats, small insertions, small deletions, small repeats, structural variant junctions, variable length tandem repeats, and/or flanking sequences, copy number variants (CNVs), transversions, gene fusions and other rearrangements are also forms of genetic variation. A variation can be a base change, insertion, deletion, repeat, copy number variation, transversion, or a combination thereof.

A cancer marker is a genetic variant associated with presence or risk of developing a cancer. A cancer marker can provide an indication a subject has cancer or a higher risk of developing cancer than an age and gender matched subject of the same species that does not have the cancer marker. A cancer marker may or may not be causative of cancer.

As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or sub-samples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular identifiers (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag each nucleic acid molecule such that different molecules can be distinguished based on their endogenous sequence information (for example, start and/or stop positions where they map to a selected reference genome, a sub-sequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, subsequences of one or both ends of a sequence, and/or lengths) and also have the same molecular barcode.

Adapters are short nucleic acids (e.g., less than 500, 100 or 50 nucleotides long) usually at least partly double-stranded for linkage to either or both ends (one adaptor on each end) of a sample nucleic acid molecule. Adapters can include primer binding sites to permit amplification of a nucleic acid molecule flanked by adapters at both ends, and/or a sequencing primer binding site, including primer binding sites for next generation sequencing (NGS). Adapters can also include binding sites for capture probes, such as an oligonucleotide attached to a flow cell support. Adapters can also include a barcode as described above. Barcodes are preferably positioned relative to primer and sequencing primer binding sites, such that a barcode is included in amplicons and sequencing reads of a nucleic acid molecule. Adapters of the same or different sequence can be linked to the respective ends of a nucleic acid molecule. Sometimes the same adapter is linked to the respective ends except that the barcode is different. A preferred adapter is a Y-shaped adapter in which one end is blunt ended or tailed as described herein, for joining to a nucleic acid molecule, which is also blunt ended or tailed with one or more complementary nucleotides and the other end of the Y-shaped adapter comprises a non-complementary sequence which does not hybridize to form a double-strand. Another preferred adapter is a bell-shaped adapter, likewise with a blunt or tailed end for joining to a nucleic acid to be analyzed.

As used herein, the term "sequencing" refers to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina or Applied Biosystems.

The phrase "next generation sequencing" or NGS refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

DNA (deoxyribonucleic acid) is a chain of nucleotides comprising four types of nucleotides based on adenine (A), thymine (T), cytosine (C), and guanine (G). RNA (ribonucleic acid) is a chain of nucleotides comprising four types of nucleotides based on A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

A "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The phrase "sequence read coverage" refers to the number of sequence reads that align to a locus of a reference sequence. "Sequence coverage information" refers to information that conveys the sequence read coverage of the given locus of the reference sequence. Sequence coverage information may include a number or identity of the sequence reads that align to the locus and/or other information that indicates the sequence read coverage at the locus.

The phrase "molecule coverage" refers to a number of molecules that cover a locus of a reference sequence. Molecules may be identified based on sequence reads and molecular barcodes described herein. As such, a molecule may be determined to cover the locus of the reference sequence based on sequence reads generated from the molecule that align to the locus.

A reference sequence is a known sequence used for purposes of comparison with experimentally determined sequences. For example, a known sequence can be an entire genome, a chromosome, or any segment thereof. A reference typically includes at least 20; 50; 100; 200; 250; 300; 350; 400; 450; 500; 1,000; 10,000; 100,000; 1,000,000; 10,000,000; 100,000,000; 1,000,000,000 or more nucleotides. A reference sequence can align with a single contiguous sequence of a genome or chromosome or can include non-contiguous segments aligning with different regions of a genome or chromosome. Reference human genomes include, e.g., hG19 and hG38.

The term "designated position" in a reference sequence refers to a genomic coordinate in the reference sequence.

A first single stranded nucleic acid sequence overlaps with a second single stranded sequence if the first nucleic acid sequence or its complement and the second nucleic acid sequence or its complement align with overlapping but non-identical segments of a contiguous reference sequence, such as the sequence of a human chromosome. A fully or partially double-stranded nucleic acid overlaps with another fully or partially double-stranded nucleic acid if either of its strands overlaps those of the other nucleic acid.

A "C" to "T" variant or conversion refers to the presence of base "T" in a sequenced polynucleotide at a coordinate position occupied in a reference sequence by base "C". A "G" to "A" variant or conversion refers to the presence of base "A" in a sequenced polynucleotide at a coordinate position occupied in a reference sequence by base "G".

A nucleic acid molecule can be conceptually divided into a 5' terminal end, an internal portion and a 3' terminal end. Terminal ends can be designated based a predetermined number of nucleotides from the terminus. For example, the 5' terminal end be represented by, e.g., the 20 terminal nucleotides to the 5' end. The 3' terminal end be represented by, e.g., the 20 terminal nucleotides to the 3' end. Alternatively, the nucleic acid molecule can be divided into a terminal portion, as described, and a remainder.

The term "minor allele frequency" ("MAF") refers to the frequency at which minor alleles (e.g., not the most common allele) occurs in a given population of nucleic acids, such as a sample.

A "tumor fraction" (TF) refers to the fraction of DNA molecules associated with a tumor in a given sample. The TF may be derived based on detecting a reduction of coverage of variant alleles in tumor cells. Lower TF in a given sample may affect the MAF of a given variant allele in the given sample, and therefore detectability of the given variant allele.

The term "Tumor Not Detected" or "TND" refers to a sample in which no somatic single nucleotide variant, insertion-deletion, copy number variant, nor fusion has been detected.

The terms "processing", "calculating", and "comparing" can be used interchangeably. The term can refer to determining a difference, e.g., a difference in number or sequence. For example, gene expression, copy number variation (CNV), indel, and/or single nucleotide variant (SNV) values or sequences can be processed.

Adapters are an artificially synthesized sequence that can be coupled to a nucleic acid molecule or a polynucleotide sequence by any approach including ligation, hybridization, and/or amplification. Adapters are short nucleic acids (e.g., less than 500, 100 or 50 nucleotides long) usually at least partly double-stranded for linkage to either or both ends of a sample nucleic acid molecule. Adapters can include primer binding sites to permit amplification of a nucleic acid molecule flanked by adapters at both ends, and/or a sequencing primer binding site, including primer binding sites for next generation sequencing (NGS). Adapters can also include binding sites for capture probes, such as an oligonucleotide attached to a flow cell support. Adapters can also include a barcode as described above. Tags are preferably position relative to primer and sequencing primer binding sites, such that a tag is included in amplicons and sequencing reads of a nucleic acid molecule. The same or different adapters can be linked to the respective ends of a nucleic acid molecule. Sometimes the same adapter is linked to the respective ends except that the tag is different. A preferred adapter is a Y-shaped adapter in which one end is blunt ended or tailed as described herein, for joining to a nucleic acid molecule, which is also blunt ended or tailed with one or more complementary nucleotides. Another preferred adapter is a bell-shaped adapter, likewise with a blunt or tailed end for joining to a nucleic acid to be analyzed.

DETAILED DESCRIPTION

FIG. 1 illustrates an example of a system 100 for training and using computer models to predict a state of genetic materials based on probabilities of each state, according to an embodiment of the disclosure. The system may process samples 101 to train one or more models 140 (illustrated as models 140a . . . n) that each output a probability that the genetic material such as a sample from an individual under test (IUT) 111 is in a specific state. In some examples, the samples 101 may include a panel of various genes of interest being studied.

For example, the system may use a model 140a to determine a probability that a sample from the IUT 111 includes a somatic homozygous deletion associated with a gene. The system may use another model 140b to determine a probability that the sample from the IUT 111 includes a somatic heterozygous deletion associated with the gene. The system may then compare the probabilities to one another to determine which one of the somatic homozygous deletion or somatic heterozygous deletion is more probable. The system may provide other types of precision diagnostics based on competing probabilities as well. For example, the system may model CNVs by modeling probabilities of different copy numbers. Based on comparisons of the output probabilities of each model (which may each correspond to a different copy number prediction), the system may determine a CNV in a sample of the IUT 111.

The system 100 may include a sequencing system 102, a computer system 110, and/or other components. It should be noted that the sequencing system 102 and the computer system 110 may be remote from one another, and connected to one another through a computer network (not illustrated). The sequencing system 102 may include a sample collection and preparation pipeline 103, a sequencing pipeline 105, and a sequence read datastore 109, and/or other components. The sequencing pipeline 105 may include one or more sequencing devices 107 (illustrated in FIG. 1 as sequencing devices 107a . . . n).

The computer system 110 may include a sequence analysis pipeline 112, a processor 120, a storage device 122, a data pre-processing subsystem 124, a classifier 130, a model validator 132, and/or other components.

The sequence analysis pipeline 112 may include a sequence quality control (QC) component 113, an alignment component 114, other analysis components 115, and an analysis QC component 116. Output from the sequence analysis pipeline 112 may be stored in an analysis datastore 117. The data pre-processing subsystem 124 may pre-process data from the sequence analysis pipeline 112 to generate training datasets 125. For instance, the training datasets 125 may include data in which tumor has not been detected ("TND") (when cancer is to be diagnosed) or otherwise normal samples (when other types of diseases or conditions are to be diagnosed) from among the samples 101. Examples disclosed throughout may refer to TND samples for illustration.

Figure 2:
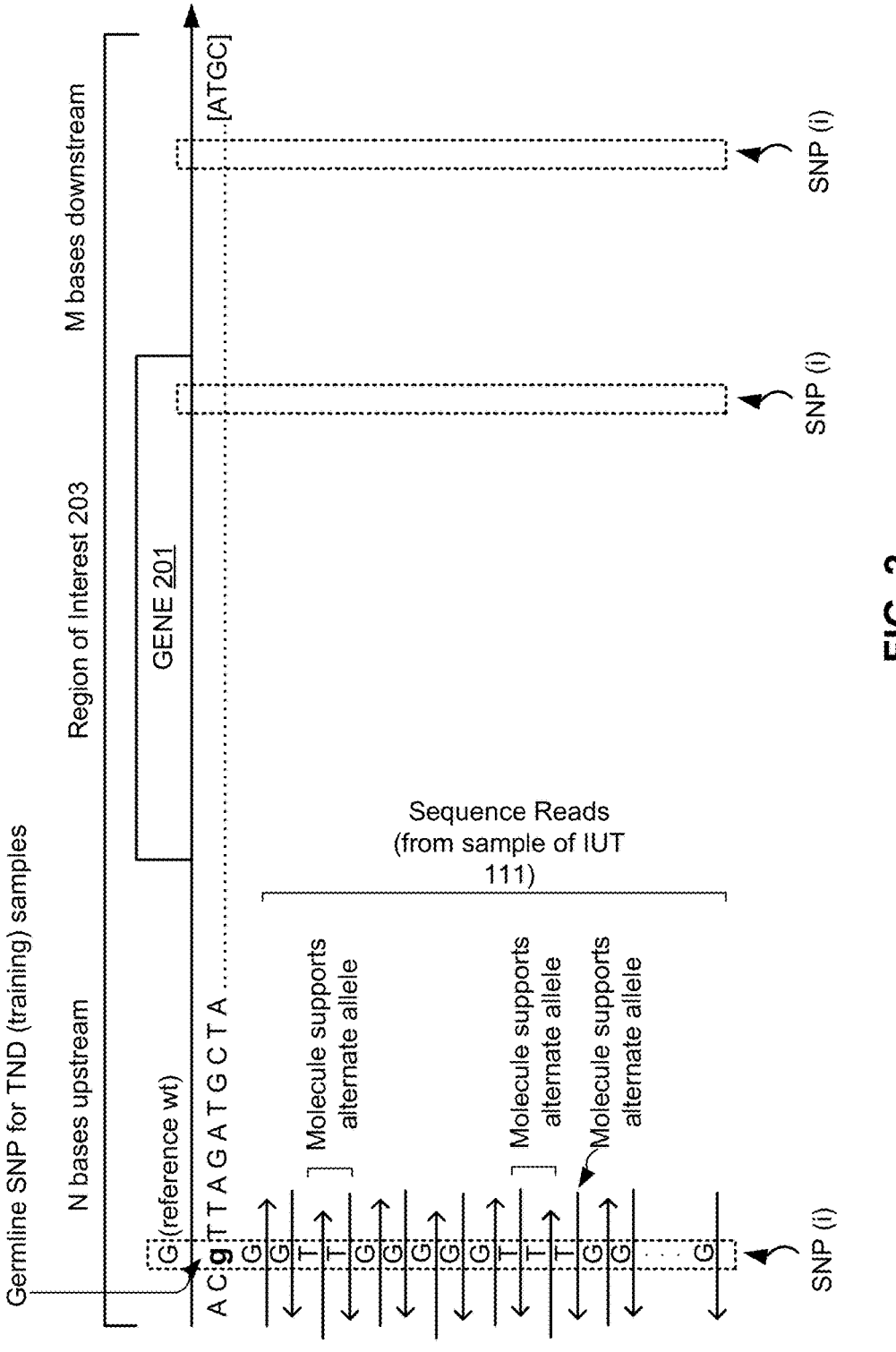
FIG. 2 illustrates a schematic diagram of determining allelic counts for germline SNPs to predict a state of a gene, according to an embodiment of the disclosure.

In some embodiments, the training datasets 125 may be stored in a training datastore 126. Reference will be made to FIG. 2 to illustrate example operations of the processor 120. FIG. 2 illustrates a schematic diagram 200 of determining allelic counts for germline SNPs to predict a state of a gene 201, according to an embodiment of the disclosure. In some examples, the processor 120 may identify germline SNPs of the TND samples for a region of interest 201 around the gene 201. In one training example, germline SNPs were selected from 28,199 samples. Out of these samples, 5105 samples (18%) were identified as having TND and were used for population allele/genotype frequencies. Germline SNPs were selected to satisfy the following conditions: (1) are within 3 Mb from selected genes (such as BRCA1, BRCA2, ATM), (2) frequency of heterozygous call (MAF>25% and MAF<75%) across 5105 TND samples is between 5% and 95%, and (3) variant is not called somatic in all 28,199 samples. The region of interest 203 may include N bases upstream from the start of the gene 201 and M bases downstream from the end of the gene 201. N and M values may be the same or different. In some examples, N and M may each be 3,000,000 nucleotides (3 Mb).

In an illustrated example of FIG. 2, a reference wildtype nucleotide at SNP site (i) (illustrated as SNP(i)) may be "G." Across the TND samples, the called nucleotide at that position may differ from one another. Because the TND samples are normal, the processor 120 may assume that the SNP(i) and other SNP sites of the TND samples do not contribute to a tumor or non-normal state. As such, these SNP sites may each serve as a reference expectation for modeling allelic counts for probabilistic determinations of the state of the gene. For instance, deviation from the observed nucleotide calls at each SNP position may indicate a probability that such deviation contributes to a particular state, such as a tumor or other non-normal state of the gene 201. The processor 120 may accordingly train the models 140 based on expectations derived from computations on data from the germline SNPs of the TND samples. Such computed data may include, for each SNP site: a prevalence of heterozygosity, a standard deviation of minor allele frequency (MAF), a genotype, a germline prevalence (priors), and/or other data.

With the expectations computed, the processor 120 may model states of the gene 201 based on sequence reads of a sample of an IUT 111 that align to the region of interest 203. For example, the processor 120 may generate competing models 140 that each output a respective score that represents a probability that the gene 201 is in a particular state. The processor 120 may compare the respective scores to compute a predictive score, which may be compared to a threshold score to determine the state of the gene 201. The processor 120 may compute the threshold score based on observed data from training samples, as will be described further below.

In some embodiments, sequence reads of molecules generated from the sample of the IUT 111 may be aligned against the reference genome to identify an allele (mutant or wildtype) that an underlying molecule supports. The sample of the IUT 111 may be prepared at the sample collection and preparation pipeline 103 and sequenced at the sequencing pipeline 105. Each molecule may be associated with sequence reads. A number of sequencing reads from a number of molecules of the sample from the IUT 111 may cover a given germline SNP site.

Based on the alignment of sequence reads generated from the sample of the IUT 111, the processor 120 may identify a number of molecules that support the SNP allele and calculate a total number of molecules. The processor 120 may model these and/or other data from the sample of the IUT 111 with the expectation data computed from each of the germline SNPs in the region of interest 203. For example, the processor 120 may generate a first output of a model 140a of allelic counts that represent a probability of a first state of the gene 201 and a second output of a model 140b of allelic counts that represent a probability of a second state of the gene 201.

The processor 120 may implement different types probabilistic distributions to generate the models 140. Furthermore, the models 140 may model various types of states of a gene 201—or more generally, the various types of states of genetic material. Attention will now turn to examples of modeling and types of states that are modeled by the processor 120.

Generally speaking, the processor 120 may implement (be programmed by) a classifier 130. Alternatively, it should be noted that the classifier 130 may include a hardware module. In any event, the classifier 130 (which may program the processor 120) may model states of a gene (such as a gene 201 illustrated in FIG. 2) based on alleles detected at a region of interest associated with the gene. More particularly, based on training datasets 125, the classifier 130 may determine one or more probabilistic models 140 (illustrated as models 140a, 140b, . . . , 140n) of specific states of the gene based on germline single nucleotide polymorphism (SNP) positions in the region of interest (such as a region of interest 203 illustrated in FIG. 2). Each model 140 may correspond to a respective probability of the state of the gene. The SNP positions may be based on sequencing reads generated by the sequencing system 102 from various samples 101. The state may include a mutational state of the gene such as, without limitation, a somatic homozygous deletion, a somatic heterozygous deletion, a copy number variation ("CNV") (including a specific copy number wildtype, gain, or loss), and/or other states of the gene.

In various embodiments, the classifier 130 may apply the models, which may be generated based on the training datasets 125, to determine the state of the gene in a sample of an individual. For example, the classifier 130 may determine probabilities that the gene in a sample of cfDNA molecules from an individual includes a somatic homozygous deletion, a somatic heterozygous deletion, and/or other state that may be correlated with a disease such as cancer or other health condition. Based on the prediction, precision treatments may be tailored for the individual. As such, the computer system 110 may be improved to provide advanced diagnostic capabilities based on non-invasive analysis of genetic material, such as cfDNA.

It is noted that although examples described herein may relate to determining gene states, the state of other genetic material such as chromosomes, exomes, and/or other genetic material may be determined as well. For instance, a CNV may be determined for chromosomes, exomes, and/or other genetic material. Having provided a description of the functionality of classifier 130, attention will now turn to more detailed examples of determining gene states by training the various models 140 and using the models 140 to predict a probability that a specific sample under test exhibits a particular gene state.

Model Training Based on TND Samples

In some embodiments, the classifier 130 use data from the samples 101. The data may include a set of samples in which Tumor is Not Detected ("TND" samples). The classifier 130 may use the TND samples to determine a prevalence of heterozygosity of each germline SNP in the TND samples and a standard deviation of minor allele frequency (MAF) of each germline SNP in the TND samples. It should be noted that variance may be used instead of standard deviation in the formula and calculations described throughout this disclosure, so long as an appropriate adjustment is made to such calculations to use variance instead of standard deviation. The prevalence of heterozygosity and the standard deviation may provide a baseline expectation of "normal" samples—that is, samples that do not exhibit disease states. The classifier 130 may also estimate germline prevalence (priors) $g_i$ for each site i. An example calculation of the prevalence of heterozygosity of each germline SNP may be given by equation (1):

$$p_a(g_i)=P(b_{ij}=a|g_i) \tag{1},$$

in which:

$p_a(g_i)$ represents the prevalence of heterozygosity of each germline SNP, $b_{ij}$ represents a set of observed bases at a SNP site i, and $g_i$ represents a genotype (AA/Aa/aa) at SNP site i.

Modeling Somatic Homozygous Deletions

The classifier 130 may generate, via a probabilistic distribution, a first model 140a of allelic counts based on one or more germline single nucleotide polymorphism (SNP) positions associated with the gene. The first model may represent (such as model) somatic homozygous deletion of the gene. For example, given the prevalence of heterozygosity of each germline SNP in the TND samples (equation (1)) and the standard deviation of MAF of each germline SNP in the TND samples, the classifier 130 may model a probability that the gene of a specific sample from an individual is associated with a somatic homozygous deletion. To do so, the classifier 130 may access a number of molecules that support existence of the somatic homozygous deletion in the gene of a sample of an IUT 111 and a total number of molecules in the sample of the IUT 111. For example, the classifier 130 may generate a model, such as model 140a, that represents a probability that a gene in a sample has a somatic homozygous deletion. In some embodiments, the classifier 130 may use a beta-binomial probabilistic distribution to generate the model 140a, although other probabilistic distributions such as a binomial probabilistic distribution, a normal (Gaussian) distribution, and/or other probabilistic modeling may be used.

The beta-binomial distribution is the binomial distribution of n Bernoulli trials in which the probability of success at each trial is fixed but randomly drawn from a beta distribution. The beta-binomial distribution may uses two parameters: $\alpha$ and $\beta$ (uniquely determined by the mean/standard deviation of the distribution). When n=1, the distribution reduces to the Bernoulli distribution. For $\alpha=\beta=1$, it is the discrete uniform distribution from 0 to n.

The binomial distribution is a probability distribution of a binomial random variable. A binomial random variable is the number of successes in N repeated trials of a binomial experiment. The binomial distribution has the following properties: the mean of the distribution ($\mu x$) is equal to $n*P$; the variance is given by: $n*P*(1-P)$; and the standard deviation ($\sigma x$) is given by equation (2):

$$\sqrt{n*P*(1-P)} \tag{2}.$$

The normal distribution The normal may be defined by the normal equation:

$$Y=\{1/[\sigma*\text{sqrt}(2\pi)]\}*e-(x-\mu)2/2\sigma2 \tag{3},$$

in which:

X is a normal random variable, $\mu$ is the mean, $\sigma$ is the standard deviation, $\pi$ is approximately 3.14159, and e is approximately 2.71828.

An example applying the beta-binomial probabilistic distribution will now be described for illustrative purposes. Those having skill in the art will understand that the binomial, normal, and/or other probabilistic distributions may be used as well based on the disclosure herein. For the beta-binomial probabilistic distribution, the classifier 130 may use the dbetabinom function in the VGAM package of the R Project, according to Equation (4):

$$P(b_{ij}|g_i|\text{TF})=P(b_{ij}|g_i)=\text{VGAM::dbetabinom}(m_i, R_i, p_a(g_i), sd(g_i)) \tag{4},$$

in which:

$m_i$ represents a number of molecules supporting the SNP allele at SNP site i, $R_i$ represents a total number of molecules, $p_a(g_i)$ represents a prevalence of heterozygosity at the SNP site i, and $sd(g_i)$ represents a standard deviation of MAF.

The classifier 130 may generate a first probabilistic output ($L_1$) of the first model 140a according to Equation (5):

$$L_1=\text{prod}(\text{sum}_{gi}(\text{prior}_{gi}*\text{dbtabinom}(m_i, R_i, p_a(g_i), sd(g_i)))) \tag{5}.$$

Modeling Somatic Heterozygous Deletions

The classifier 130 may generate, via a probabilistic distribution, a second model 140b of allelic counts in the sample based on the one or more germline SNP positions. The second model 140b may represent (such as model) somatic heterozygous deletion of the gene. Because detection of heterozygous deletions may be affected by the TF, the classifier 130 may determine the mean, mu.tf (which may also be notated $\mu$.tf), and standard deviation, sd.tf (which may also be notated $\sigma$.tf), of the TF based on coverage of reads (sequence read coverage) in a sample of the IUT 111.

In some embodiments, the classifier 130 may use a beta-binomial probabilistic distribution to generate the model 140b, although other probabilistic distributions such as a binomial probabilistic distribution, Gaussian distribution, and/or other probabilistic modeling may be used.

For the beta-binomial probabilistic distribution, the classifier 130 may use the dbetabinom function in the VGAM package of the R Project, according to Equation (6):

$$P(b_{ij}|g_i|\text{TF})=P(b_{ij}|g_i)=\text{VGAM::dbetabinom}(m_i, R_i, mu_i, sd_i) \tag{6},$$

in which:

$m_i$ represents a number of molecules supporting the SNP allele at SNP site i, $R_i$ represents a total number of molecules, $mu_i$ represents a mean of TF calculated for a sample of the IUT 111, and $sd_i$ represents a standard deviation of TF calculated for the sample of the IUT 111.

The classifier 130 may generate a second probabilistic output $L_0$ of the second model 140b according to Equation (5):

$$L_0=\text{prod}(\text{sum}_{gi}(\text{prior}_{gi}*\text{dbtabinom}(m_i, R_i, m_i(g_i), sd_i(g))) \tag{7},$$

in which:

$m_i(g_i)=pa(g_i)$ if $g_i$=AA or aa;

$1-m.tf*p_a(g_i=Aa)+m.tf*\max(p_a(g_i=aa), p_a(g_i=AA))$, $\text{sd}_i(g_i)=\text{sd}(g_i)$, if gi=AA or aa
    var_prod(sd.tf, 1-mf.tf, sd $(g_i$=Aa), $p_a(g_i$=Aa))+
    var_prof(sd.tf, m.tf, sd $(g_i$=aa), $p_a(g_i$=aa))
    where var_prod(va, ma, vb, mb)=va*vb+va*mb$^2$+
    vb*ma$^2$ It should be noted that the first model 140*a* and the second model 140*b* need not be use the same probabilistic distribution so long as the first model 140*a* and the second model 140*b* each output a probability.

The classifier 130 may compare the first probabilistic output of the first model 140*a* and the second probabilistic output of the second model 140*b* to determine which probabilistic output is more likely. For example, the classifier 130 may determine whether a somatic homozygous deletion or a somatic heterozygous deletion is more likely. In a particular example, the classifier 130 may use a log likelihood ratio ("LLR") to generate an LLR score based on the first probabilistic output (probability of somatic homozygous deletion) and the second probabilistic output (probability of somatic heterozygous deletion). In some embodiments, one of the first or second probability output may be used as a null probability such that if the LLR score does not exceed a threshold cutoff score, the null probability is rejected. For example, the classifier 130 may compare the LLR score to the threshold cutoff score to determine whether the second probability output should be rejected. In other words, if the LLR score exceeds threshold cutoff score, then the classifier 130 may determine that the first probability output should be selected. In this example, the classifier 130 may generate a prediction that the somatic homozygous deletion for the gene exists in the sample of the IUT 111 based on the comparison.

In some examples, in order to mitigate errors, the model 140A or 140B may be used to determine a sample genotype for each SNP overlapping a given gene. If none of the germline SNPs is determined to be heterozygous, that the given gene may be labeled as a 'no call' and no somatic homozygous or heterozygous deletion is associated to the given gene.

Learning Threshold Score Cutoffs

Figure 10B:
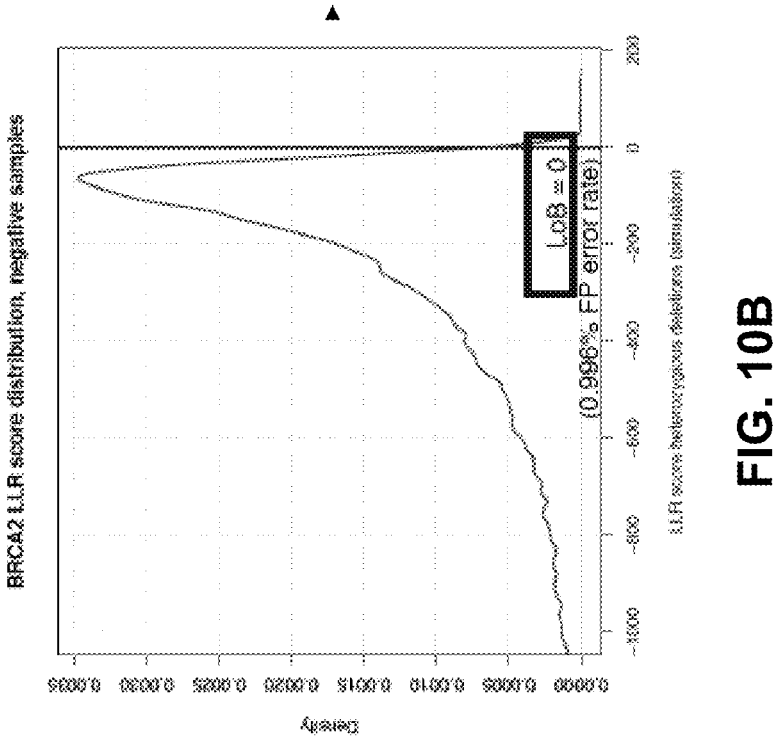
FIG. 10B illustrates an example plot of LLR score distribution for BRCA2 negative samples, according to an embodiment of the disclosure.
Figure 10A:
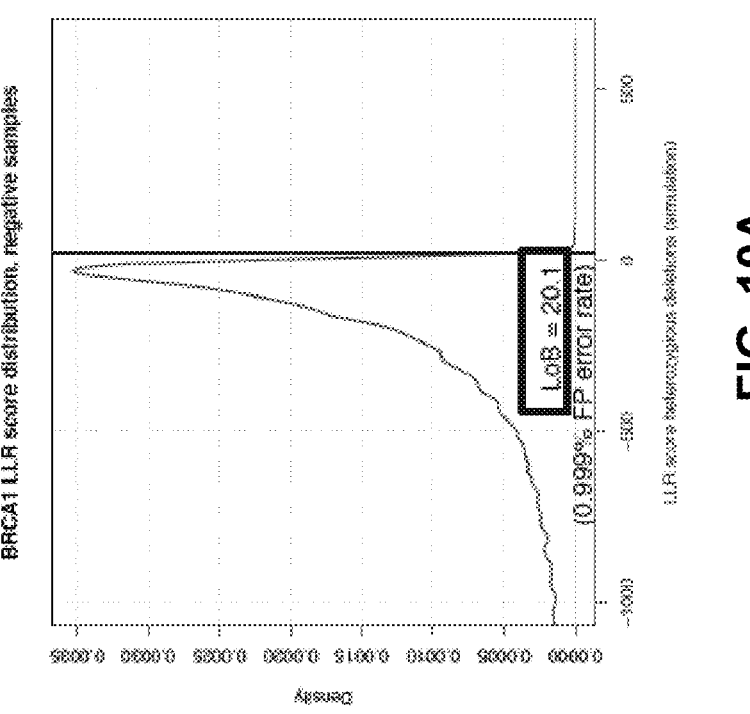
FIG. 10A illustrates an example plot of LLR score distribution for BRCA1 negative samples, according to an embodiment of the disclosure.

In some embodiments, the threshold cutoff score may be customized for different genes or other genetic material being assayed. For example, the BRCA1 gene may be associated with a different threshold cutoff score than the BRCA2 gene. Other genes may be similarly associated with custom threshold cutoff score. In these embodiments, the classifier 130 may be trained to determine the threshold cutoff score. In some of these embodiments, the classifier 130 may be trained to determine the threshold cutoff score for a specific gene. For example, the classifier 130 may be trained using simulations of somatic heterozygous deletions starting from the TND samples. Referring to FIGS. 10A and 10B, for example, the limit of blank (LoB), or highest LLR score expected to be found when no homozygous deletions are present for BRCA1 and BRCA2 negative samples. Referring to FIGS. 10A and 10B, 100,000 cases of somatic heterozygous deletions starting from the TND samples were simulated. The TF distribution observed in 28,000 samples was used as the TF for determining the LoB for BRCA1 and BRCA2. As illustrated, the threshold cutoff score for comparison with the LLR score is 20.1 and 0 for BRCA1 and BRCA2, respectively. Thus, if a somatic deletion of BRCA1 is observed in a sample of the IUT 111, and the LLR score for BRCA1 in the sample of the IUT 111 is >20.1, then the classifier 130 may predict that the somatic deletion is a somatic homozygous deletion. Similarly, if a somatic deletion of BRCA1 is observed in a sample of the IUT 111, and the LLR score for BRCA2 in the sample of the IUT 111 is >0, then the classifier 130 may predict that the somatic deletion is a somatic homozygous deletion. It should be noted that other genes may be similarly simulated to determine the threshold cutoff score.

In some embodiments, the model validator 132 may use simulated and/or clinical data to validate results of the models 140. For instance, the model validator 132 may consult a diagnostic result datastore 150 and/or a clinical results datastore 160 to validate predications. For simulated results, panels of known samples may be modeled to generate predictions of the state of genetic materials of these samples. These results may be used to validate the results of prior predictions and/or future predictions.

Figure 3:
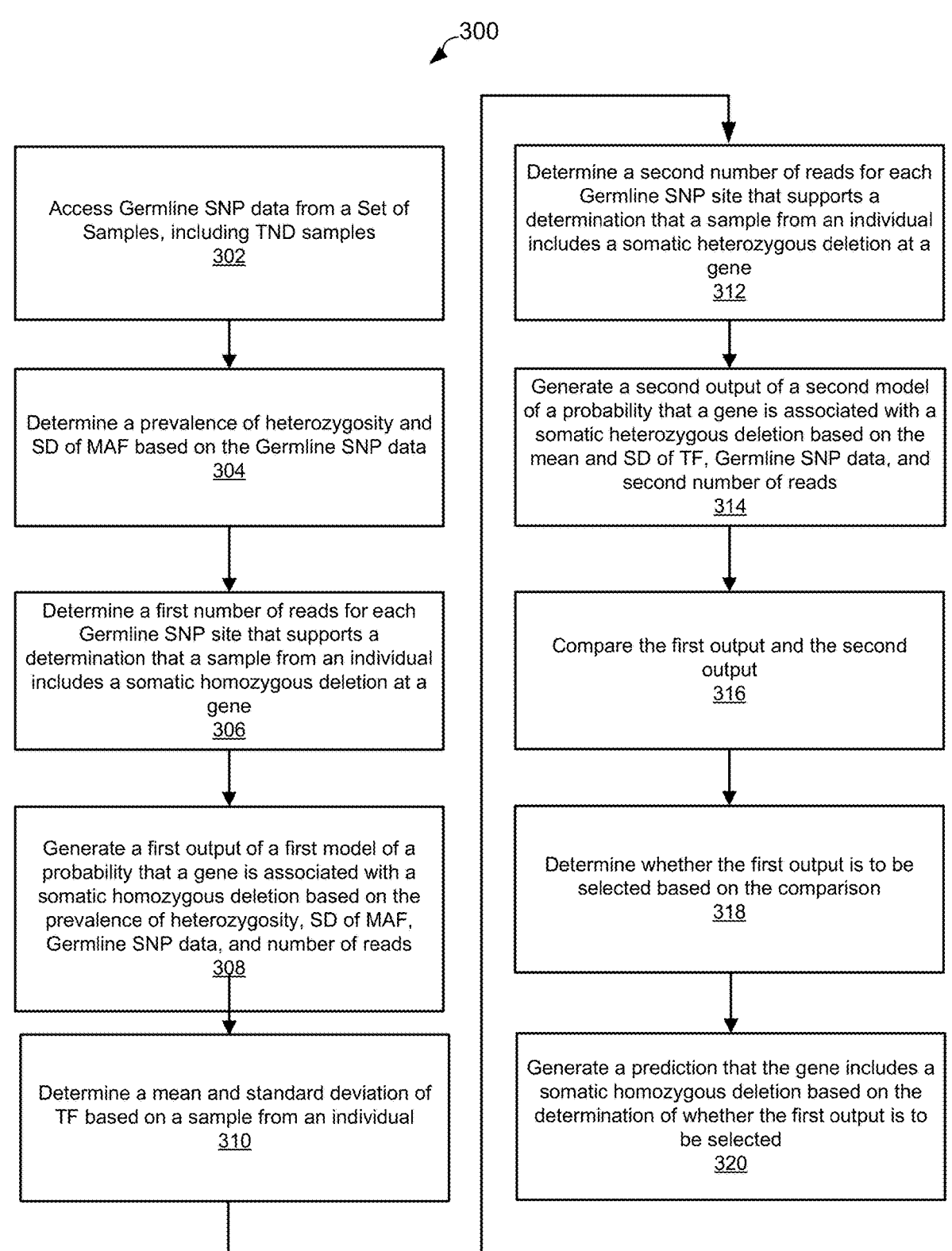
FIG. 3 illustrates a process of predicting somatic homozygous or heterozygous deletions based on trained models, according to an embodiment of the disclosure.

FIG. 3 illustrates a process 300 of predicting somatic homozygous or heterozygous deletions based on trained models, according to an embodiment of the disclosure. The process 300 is provided by way of example, as there may be a variety of ways to carry out the method described herein. Although the process 300 is primarily described as being performed by the computer system 110 (via the processor 120) illustrated in FIG. 1, the process 300 may be executed or otherwise performed by other systems, or a combination of systems. Each block shown in FIG. 3 may further represent one or more processes, methods, or subroutines, and one or more of the blocks may include machine-readable instructions stored on a non-transitory computer readable medium and executed by a processor or other type of processing circuit to perform one or more operations described herein. The various operations of the process 300 disclosed herein, or the blocks carried out by the systems disclosed herein, may be carried out at the same or different times, in the same or different geographical locations, e.g. countries, and/or by the same or different people.

In an operation 302, the processor 120 may access germline SNP data from a set of samples, including the TND samples. In an operation 304, the processor 120 may determine a prevalence of heterozygosity and SD of MAF based on the Germline SNP data. In an operation 306, the processor 120 may determine a first number of reads for each Germline SNP site that supports a determination that a sample from an individual includes a somatic homozygous deletion at a gene.

In an operation 308, the processor 120 may generate a first output of a first model of a probability that a gene is associated with a somatic homozygous deletion based on the prevalence of heterozygosity, standard deviation (sd) of MAF, Germline SNP data, and number of reads. In an operation 310, the processor 120 may determine a mean and standard deviation of TF based on a sample from an individual. In an operation 312, the processor 120 may determine a second number of reads for each Germline SNP site that supports a determination that a sample from an individual includes a somatic heterozygous deletion at a gene. In an operation 314, the processor 120 may generate a second output of a second model of a probability that a gene is associated with a somatic heterozygous deletion based on the mean and SD of TF, Germline SNP data, and second number of reads. In an operation 316, the processor 120 may compare the first output and the second output. In an operation 318, the processor 120 may determine whether the first output is to be selected based on the comparison. In an operation 320, the processor 120 may generate a prediction that the gene includes a somatic homozygous deletion based on the determination of whether the first output is to be selected.

Figure 9B:
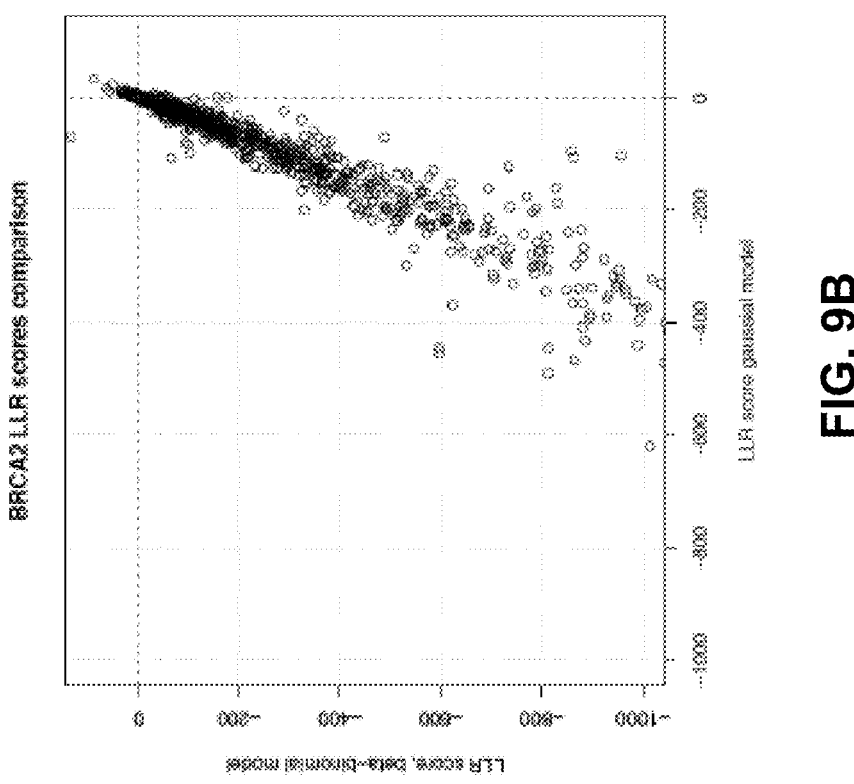
FIG. 9B illustrates an example plot of score comparisons between a beta-binomial model and a Gaussian model for the BRCA2 panel, according to an embodiment of the disclosure.
Figure 9A:
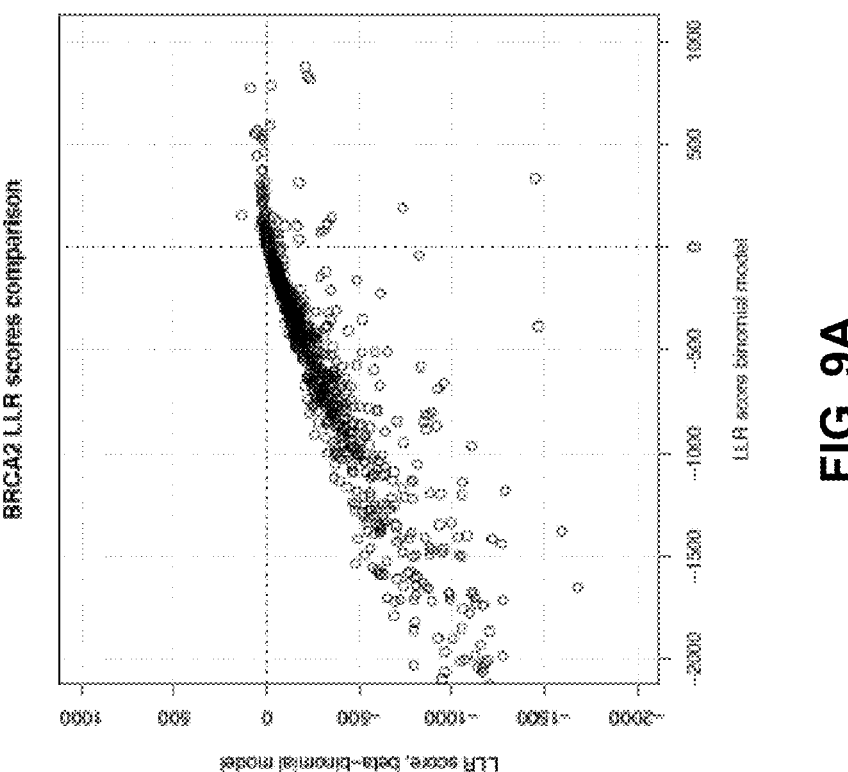
FIG. 9A illustrates an example plot of score comparisons between a beta-binomial model and a binomial model for the BRCA2 panel, according to an embodiment of the disclosure.

The classifier 130 may apply various modeling techniques to predict the state of the gene. The classifier 130 may use other modeling techniques as well. For instance, FIGS. 9A and 9B illustrate a comparison of results of different modeling techniques. Others probabilistic techniques may be used as well.

Modeling Other Types of States of Genetic Material

Figure 4:
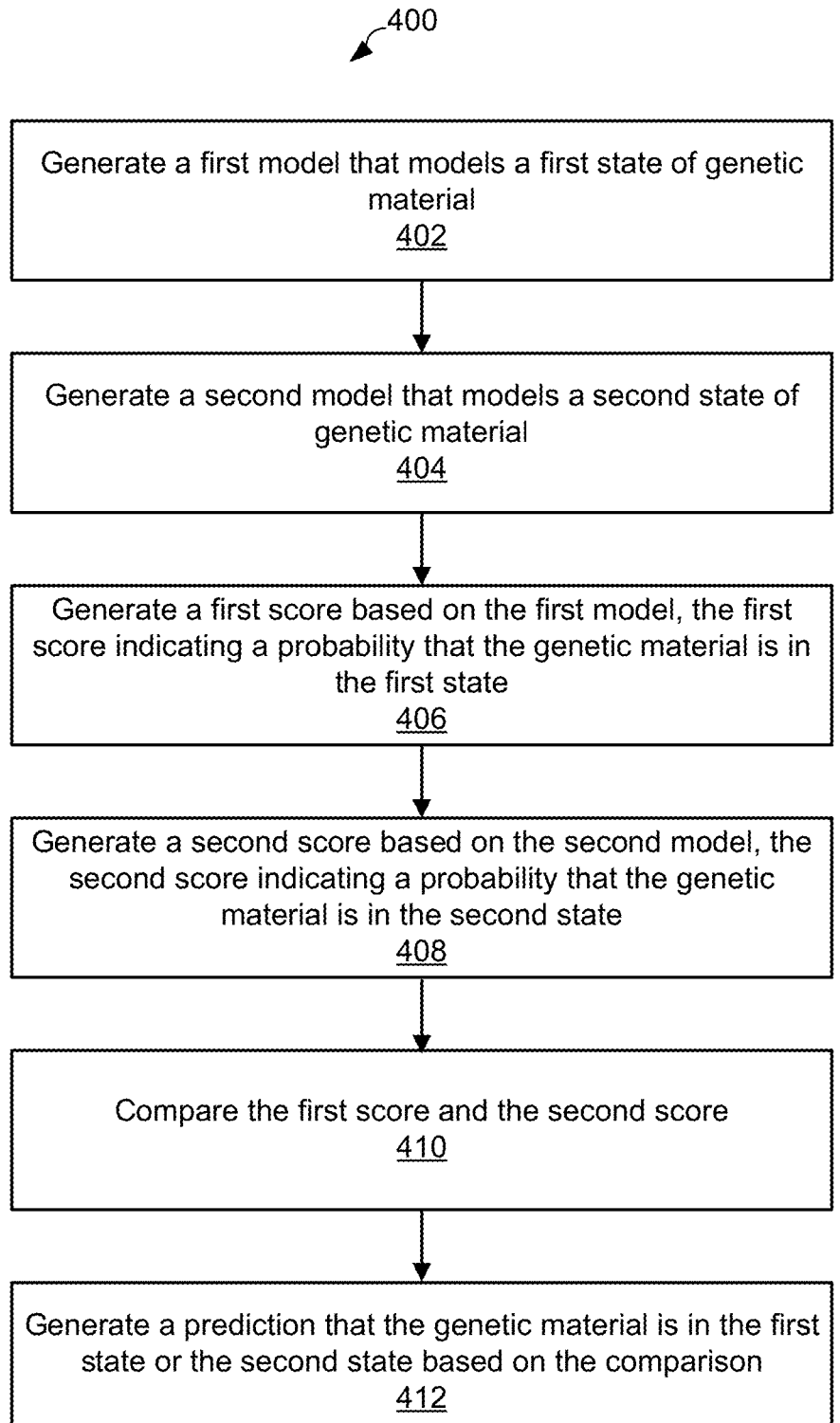
FIG. 4 illustrates a process of predicting a state of genetic material based on trained models, according to an embodiment of the disclosure.

The classifier 130 may model other types of states of genetic material. For instance, the classifier 130 may predict various types of states of genetic material such as CNVs. Reference will now be made to FIG. 4, which illustrates a process 400 of predicting a state of a genetic material. The process 400 is provided by way of example, as there may be a variety of ways to carry out the method described herein. Although the method 400 is primarily described as being performed by the computer system 110 (via the processor 120) illustrated in FIG. 1, the process 400 may be executed or otherwise performed by other systems, or a combination of systems. Each block shown in FIG. 4 may further represent one or more processes, methods, or subroutines, and one or more of the blocks may include machine-readable instructions stored on a non-transitory computer readable medium and executed by a processor or other type of processing circuit to perform one or more operations described herein. The various operations of the process 400 disclosed herein, or the blocks carried out by the systems disclosed herein, may be carried out at the same or different times, in the same or different geographical locations, e.g. countries, and/or by the same or different people.

Examples described with respect to FIG. 4 include determining a CNV in a sample of the IUT 111. More specifically, examples may be used to determine copy number variance (such as amplification) in genetic material from a sample of an IUT 111. However, other types of states of genetic materials may be determined in a similar manner, using alternative (competing) probabilities of different states and selecting a most likely probability.

In an operation 402, the processor 120 may generate a first model that models a first state of genetic material. The first state may include a first CNV or other state. In an operation 404, the processor 120 may generate a second model that models a second state of the genetic material. The second state may include a second CNV or other state. In an operation 406, the processor 120 may generate a first score based on the first model. The first score may indicate a probability that the genetic material is in the first state.

In an operation 408, the processor 120 may generate a second score based on the second model. The second score may indicate a probability that the genetic material is in the second state. In an operation 410, the processor 120 may compare the first score and the second score. In an operation 412, the processor 120 may generate a prediction that the genetic material is in the first state or the second state based on the comparison.

Similar to the way in which the MAF relating to the germline SNPs was used by the classifier 130 to generate probabilities of somatic heterozygous and somatic homozygous deletions, the MAF may be used to resolve probabilities of CNV. For example, the MAF of a germline SNP in a sample in which no CNV has been detected may be used to determine whether reads in a sample support a specific amplification.

Figure 5:
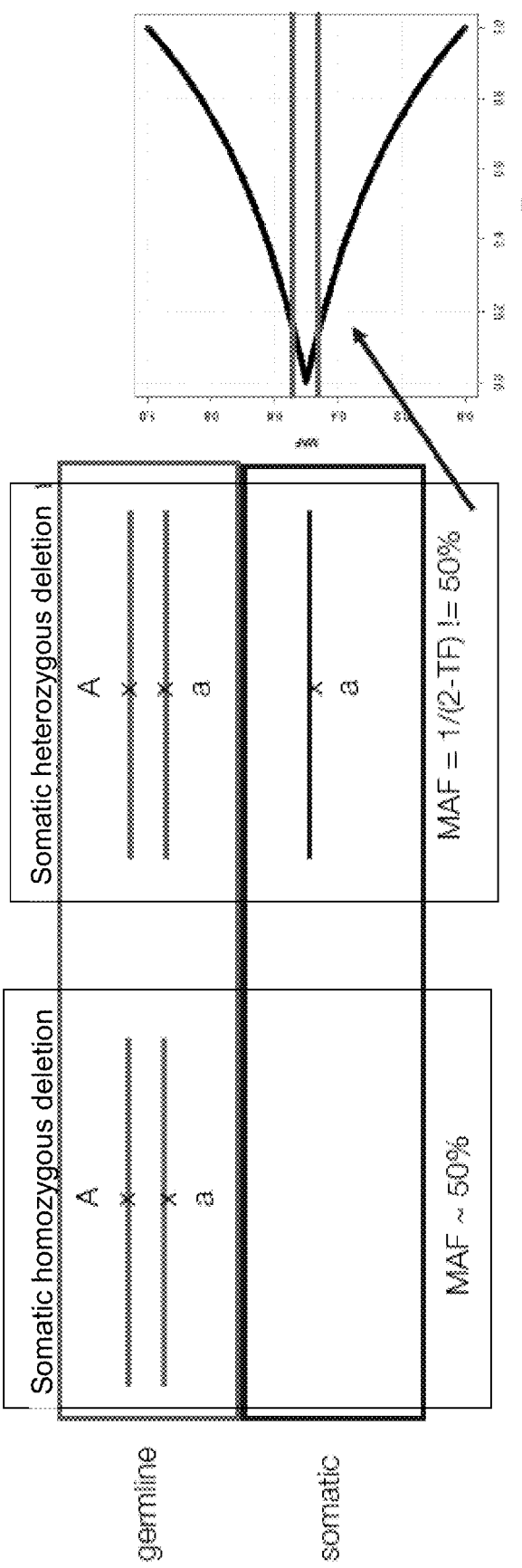
FIG. 5 illustrates types of somatic deletions, according to an embodiment of the disclosure.

FIG. 5 illustrates types of somatic deletions, according to an embodiment of the disclosure. Somatic homozygous deletions can be produced in 2 ways: (1) germline cells have a single copy of the gene, and somatic cells acquire the second deletion (LoD similar to single copy amplification detection). These may be detected based on coverage+no heterozygous SNPs overlapping. In some instances, though these have not been observed, germline cells may have no copies of the gene. (2) The second way in which somatic homozygous deletions may be produced is that germline cells have 2 copies of the gene, and somatic cells lose both copies (this scenario has been observed in higher prevalence). In some embodiments, for biallellic somatic copy number loss, in a mixture of germline and somatic cells, the reference allele frequency of a germline heterozygous SNP is 0.5. In the case of somatic LOH, the reference allele frequency is 0.5–0.5*TF (tumor fraction) or 0.5+0.5*TF, depending if the reference allele is lost or retained in cancer cells. In some embodiments, for LOH, the expected allele frequency may depend on the fraction of tumor cells. Thus, the system may distinguish between LOH and biallellic copy number loss based on the calculated allele frequency as compared to the expected allele frequency of 0.5.

FIG. 6A illustrates example plots 600(A)(1) and 600(A) (2) of a BRCA1 homozygous deletion, according to an embodiment of the disclosure. FIG. 6B illustrates example plots 600(A)(1) and 600(A)(2) of a BRCA2 heterozygous deletion, according to an embodiment of the disclosure. Referring to plots 600(A)(1) and 600(B)(1), for a given cfDNA sample, the normalized molecule coverage (y-axis) is represented across targeting probes (x-axis) sorted by genomic location. Chromosomal separation is represented by vertical lines and identifiers presented in the bottom line of the plots. Regions with no somatic copy number changes show molecule coverage close to 2, while somatic deletions can be identified by molecule coverage levels below 2. Referring to plots 600(B)(1) and 600(B)(2), for the same sample, the MAFs (y-axis) of known germline SNPs are represented against their genomic location (x-axis). A somatic deletion, as observed in coverage plots of the top rows, manifests in germline variants MAFs close to 50% (see plots illustrated in FIG. 6A) while heterozygous deletions produce imbalanced germline variants MAFs (see plots illustrated in FIG. 6B).

Figure 7B:
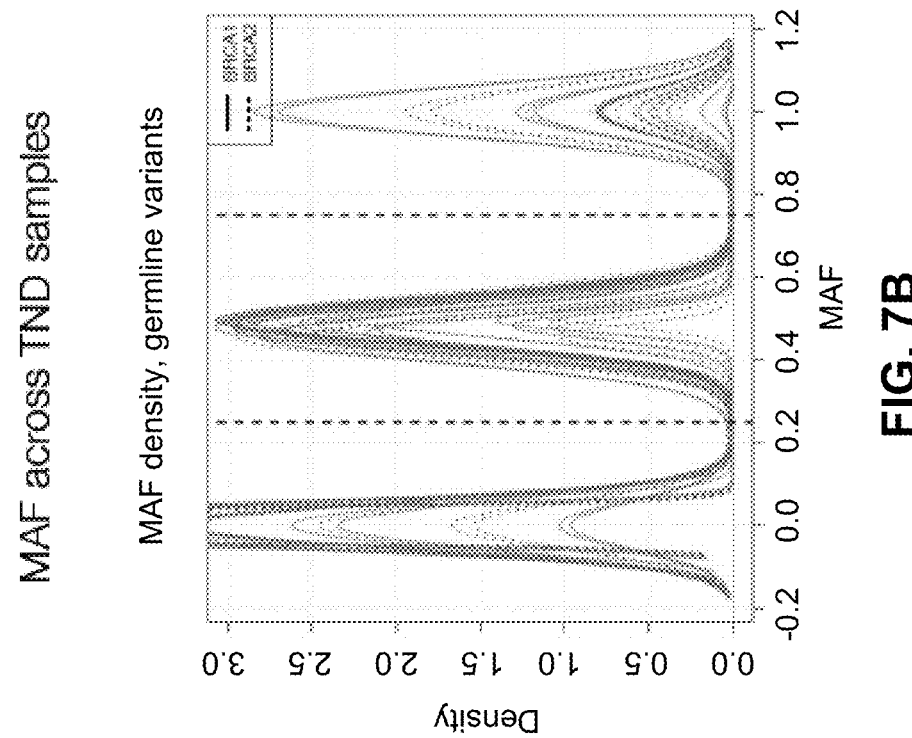
FIG. 7B illustrates an example plot of a MAF across TND samples, according to an embodiment of the disclosure.
Figure 7A:
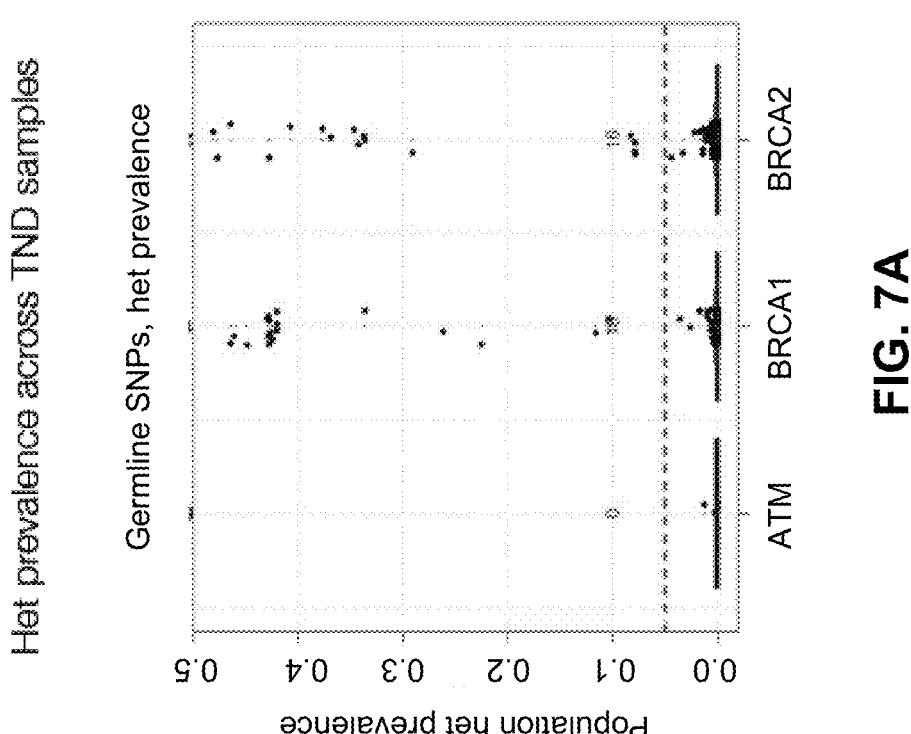
FIG. 7A illustrates an example plot of het prevalence in TND samples, according to an embodiment of the disclosure.

FIG. 7A illustrates an example plot of heterozygous genotype prevalence, for known germline SNPs overlapping ATM, BRCA1 and BRCA2 genes, observed in TND samples, according to an embodiment of the disclosure. FIG. 7B illustrates an example plot of a MAF across TND samples, according to an embodiment of the disclosure.

Figure 8B:
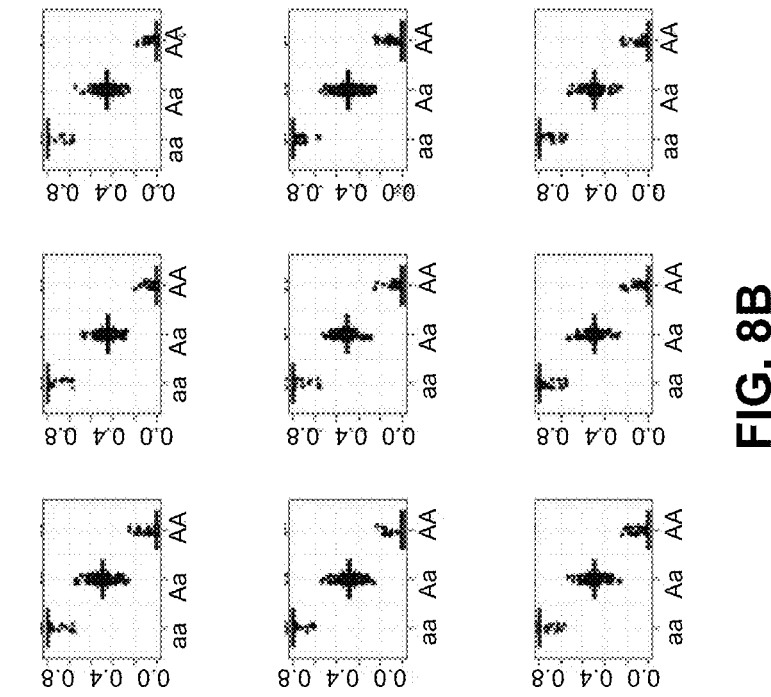
FIG. 8B illustrates an example plot of MAF values for BRCA2, according to an embodiment of the disclosure.
Figure 8A:
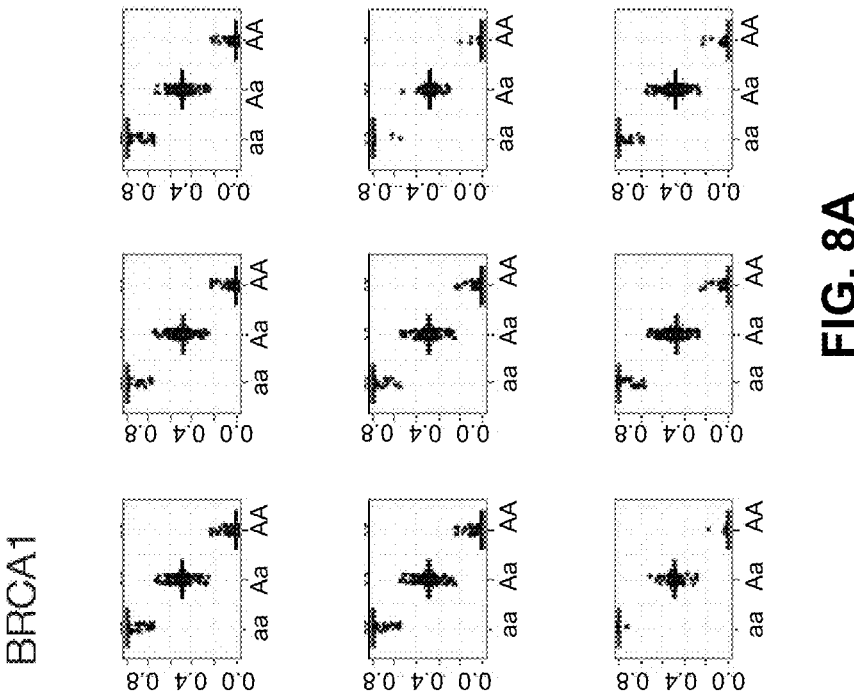
FIG. 8A illustrates an example plot of MAF values for BRCA1, according to an embodiment of the disclosure.

FIG. 8A illustrates an example plot of MAF values for BRCA1, according to an embodiment of the disclosure. FIG. 8B illustrates an example plot of MAF values for BRCA2, according to an embodiment of the disclosure. FIGS. 8A and 8B show examples of MAF (y-axis) of 9 known germline SNVs for the 3 possible genotypes of each SNP (homozygous alternative allele/heterozygous/homozygous reference allele) (x-axis). FIG. 9A illustrates an example plot of score comparisons between a beta-binomial model and a binomial model for the BRCA2 panel, according to an embodiment of the disclosure. FIG. 9B illustrates an example plot of score comparisons between a beta-binomial model and a Gaussian model for the BRCA2 panel, according to an embodiment of the disclosure. FIG. 10A illustrates an example plot of LLR score distribution for BRCA1 negative samples, according to an embodiment of the disclosure. FIG. 10B illustrates an example plot of LLR score distribution for BRCA2 negative samples, according to an embodiment of the disclosure.

Figure 11B:
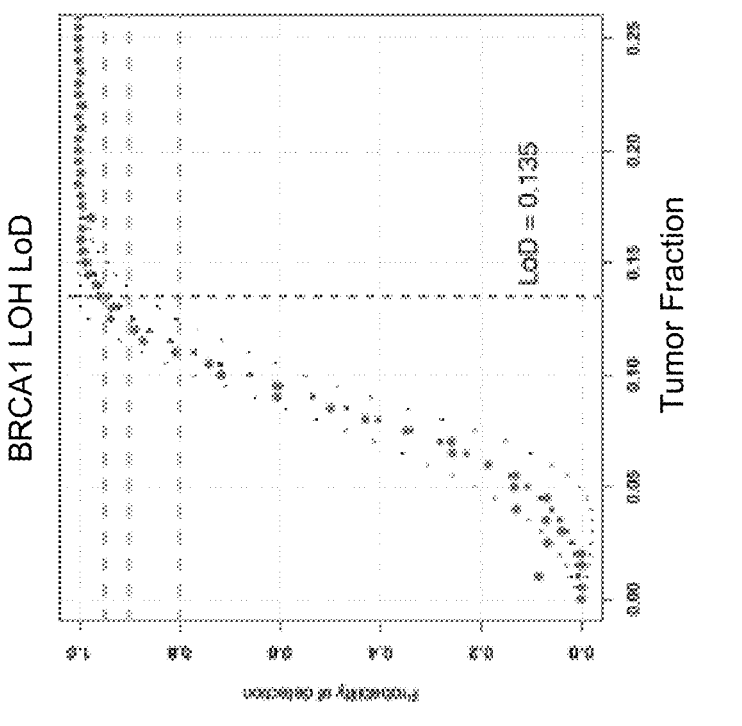
FIG. 11B illustrates an example plot of LoD HRR homozygous deletion for BRCA1, according to an embodiment of the disclosure.
Figure 11A:
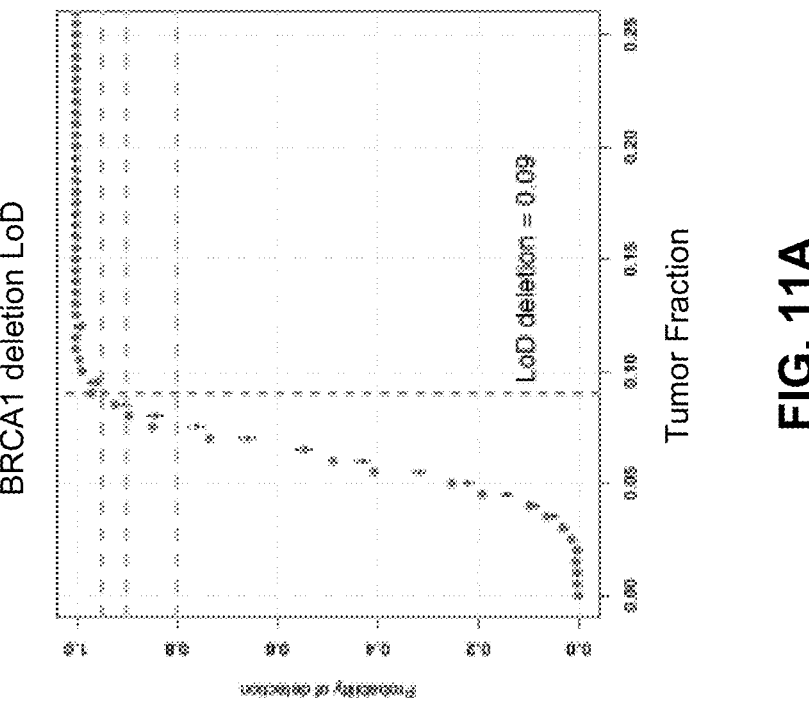
FIG. 11A illustrates an example plot of Limit of Detection (LoD) deletion for BRCA1, according to an embodiment of the disclosure.

FIG. 11A illustrates an example plot of LoD of deletion for BRCA1, according to an embodiment of the disclosure. FIG. 11B illustrates an example plot of LoD of Loss of Heterozygosity (LOH) (interchangeably referred to herein as "heterozygous deletion") for BRCA1, according to an embodiment of the disclosure. Simulations: 100 k cases of homozygous somatic deletions starting from TND samples.

TF used=TF distribution observed in 28,199 samples. LoD depends on the 2 factors (the 2-step algorithm): (1) Deletion detection sensitivity (coverage based only): BRCA1 amplification/deletion mean cut off=0.05; and (2) Ability to discriminate between homozygous and heterozygous somatic deletions (LLR test).

Figure 12B:
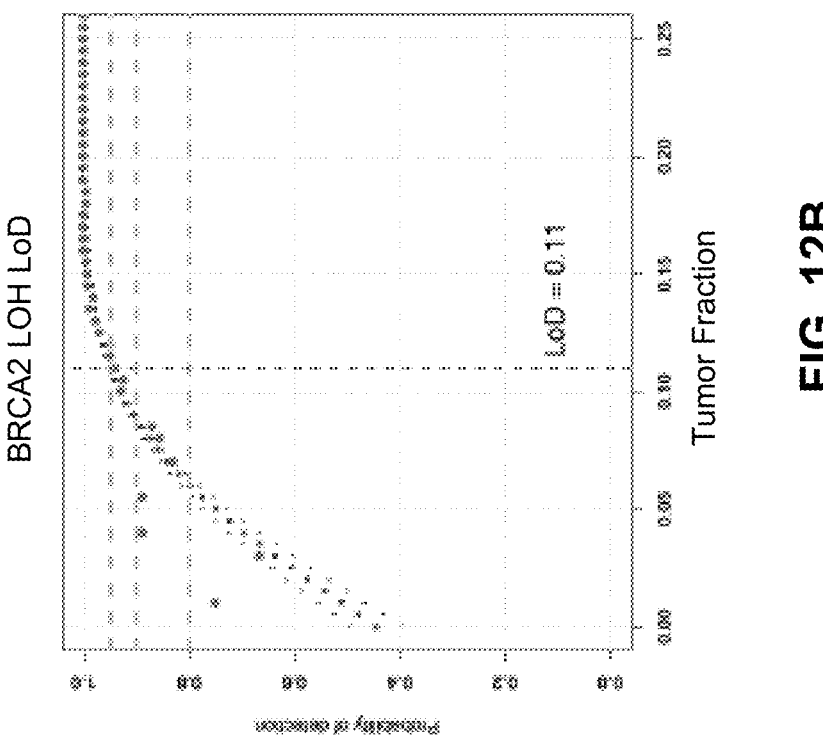
FIG. 12B illustrates an example plot of LoD HRR homozygous deletion for BRCA2, according to an embodiment of the disclosure.
Figure 12A:
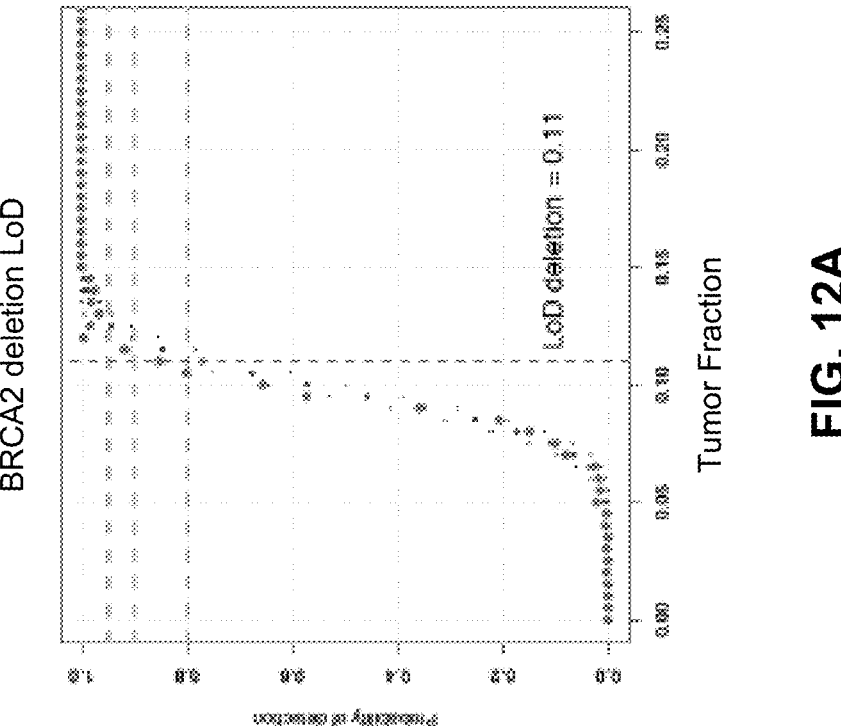
FIG. 12A illustrates an example plot of LoD deletion for BRCA2, according to an embodiment of the disclosure.

FIG. 12A illustrates an example plot of LoD of deletion for BRCA2, according to an embodiment of the disclosure. FIG. 12B illustrates an example plot of LoD of LOH for BRCA2, according to an embodiment of the disclosure. Simulations: 100 k cases of homozygous somatic deletions starting from TND samples.

TF used=TF distribution observed in 28,199 samples.

LoD depends on the 2 factors (the 2-step algorithm): (1) Deletion detection sensitivity (coverage based only): BRCA2 amplification/deletion mean cut off=0.09; and (2) Ability to discriminate between homozygous and heterozygous somatic deletions (LLR test).

Figure 13:
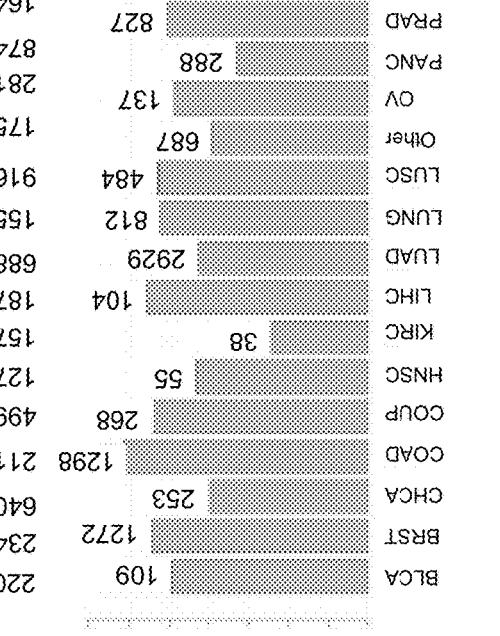
FIG. 13 illustrates example plots of prevalence of TF vs cancer type, according to an embodiment of the disclosure.

FIG. 13 illustrates example plots of prevalence of TF vs cancer type, according to an embodiment of the disclosure.

Figure 14:
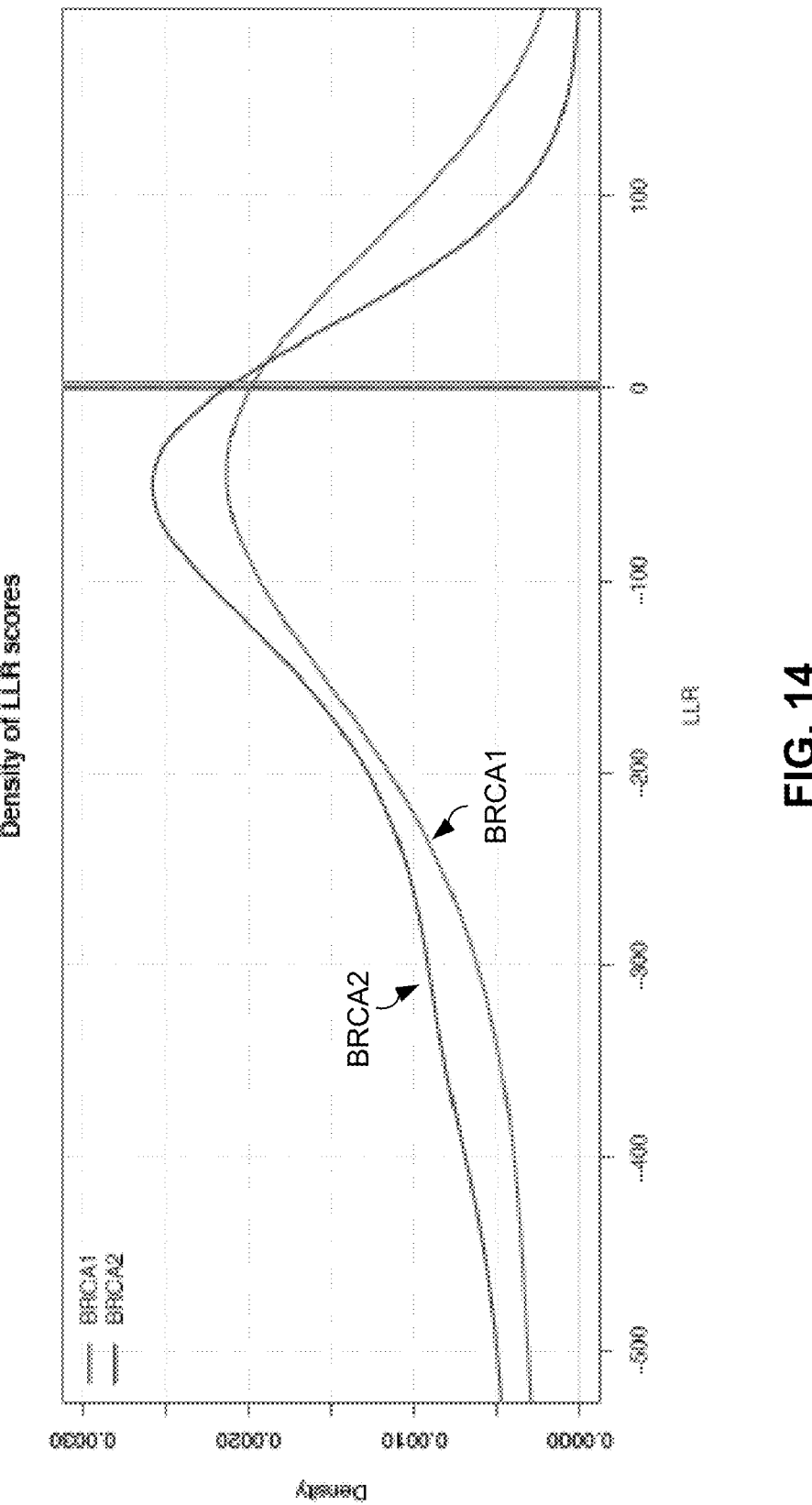
FIG. 14 illustrates an example plot of density of LLR scores for BRCA1 and BRCA2, according to an embodiment of the disclosure.

FIG. 14 illustrates an example plot of density of LLR scores for BRCA1 and BRCA2, according to an embodiment of the disclosure. A set of 28,000 training samples were randomly selected, with cutoffs of 2.5 and 0 (determined in LoB part) to call a sample with BRCA1/2 homozygous deletion. 387 and 994 samples showed somatic deletions for BRCA1 and BRCA2, respectively. Out of these samples, 49 and 60 were called to have homozygous deletions of BRCA1 and BRCA2, respectively.

Figure 15:
FIG. 15 illustrates example charts of the prevalence of BRCA2 homozygous deletions, according to an embodiment of the disclosure.
Figure 15:
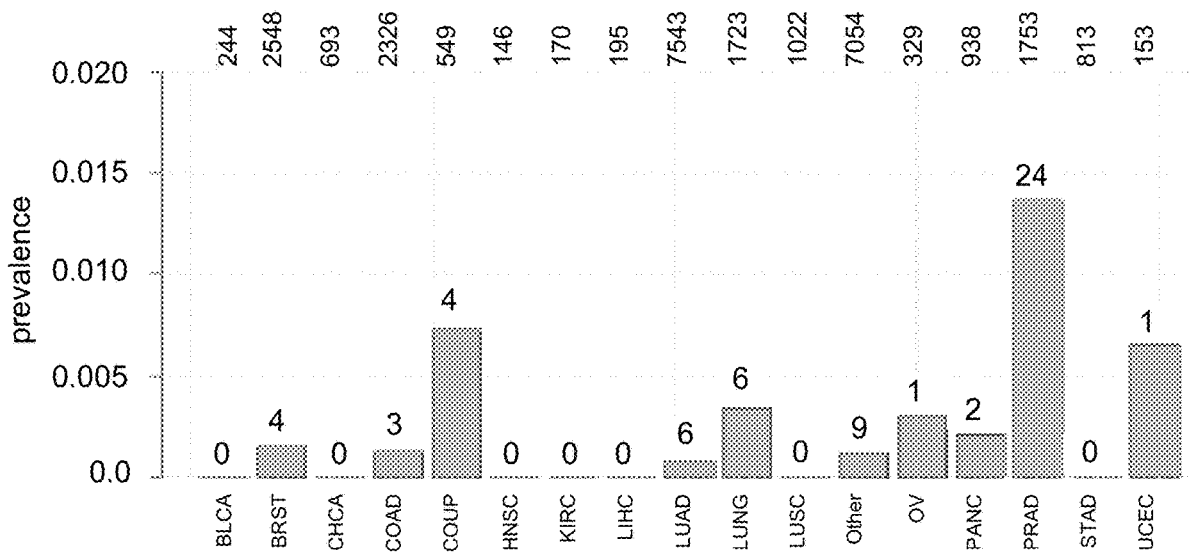
Figure 15:
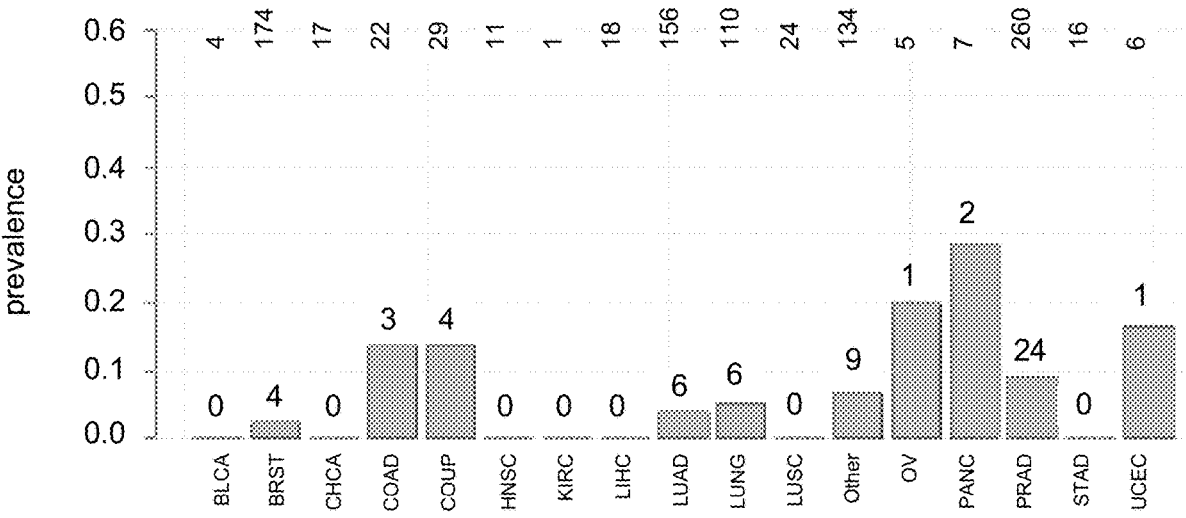
Figure 16:
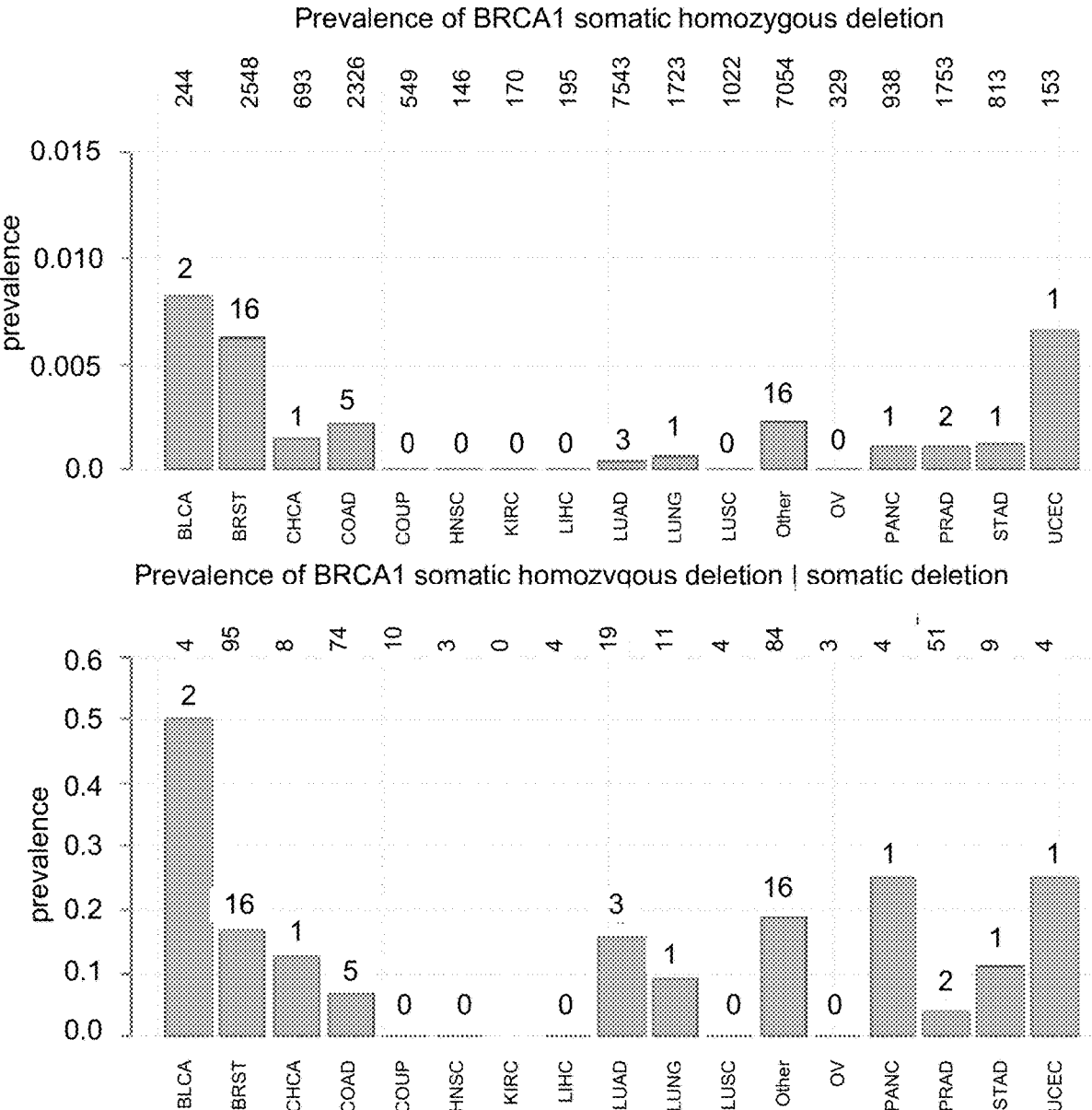
FIG. 16 illustrates example charts of the prevalence of BRCA1 homozygous deletions, according to an embodiment of the disclosure.
Figure 17:
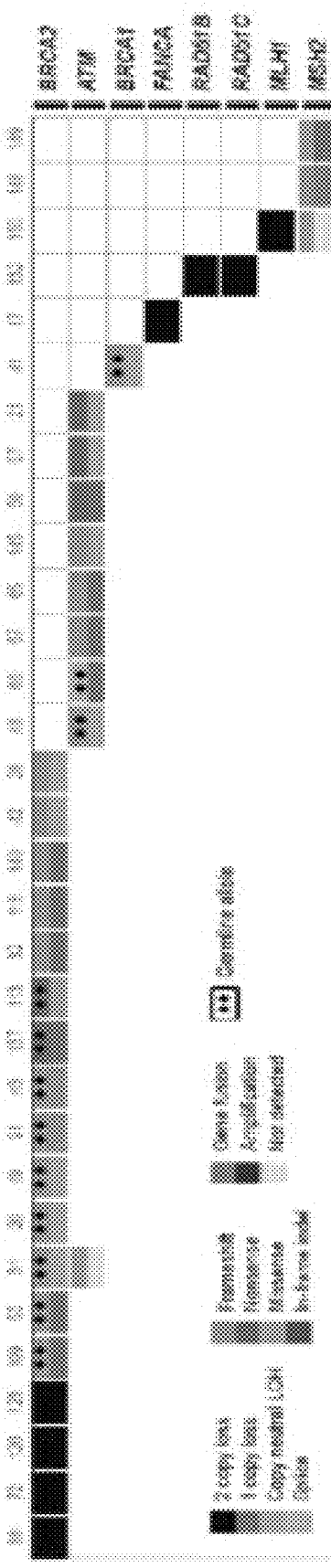
FIG. 17 illustrates example of homozygous deletion of BRCA2 and potential clinical actionability, according to an embodiment of the disclosure.

FIG. 15 illustrates example charts of the prevalence of BRCA2 homozygous deletions observed in multiple cancer type populations, according to an embodiment of the disclosure. FIG. 16 illustrates example charts of the prevalence of BRCA1 homozygous deletions observed in multiple cancer type populations, according to an embodiment of the disclosure. FIG. 17 illustrates example of homozygous deletion of BRCA2 and potential clinical actionability, according to an embodiment of the disclosure. The plot illustrated in FIG. 17 is from "Integrative clinical genomics of advanced prostate cancer," *Cell* 161: 1215-1228 (2015), by Robinson D, Van Allen E M, Wu Y M, Schultz N, Lonigro R J, Mosquera J M, Montgomery B, Taplin M E, Pritchard C C, Allard G, et al. ("Robinson"), which is incorporated by reference in its entirety herein. Robinson shows: an integrative analysis of both the somatic and pathogenic germline alterations in BRCA2 identified 19/150 (12.7%) of cases with loss of BRCA2, of which approximately 90% exhibited biallelic loss. This was commonly a result of somatic point mutation and loss of heterozygosity, as well as homozygous deletion. A clinical trial evaluating poly(ADP-ribose) polymerase (PARP) inhibition in unselected mCRPC affected individuals is showing that multiple affected individuals in this trial who experienced clinical benefit harbored biallelic BRCA2 loss, providing further evidence of clinical actionability.

Figures 18A, 18B:
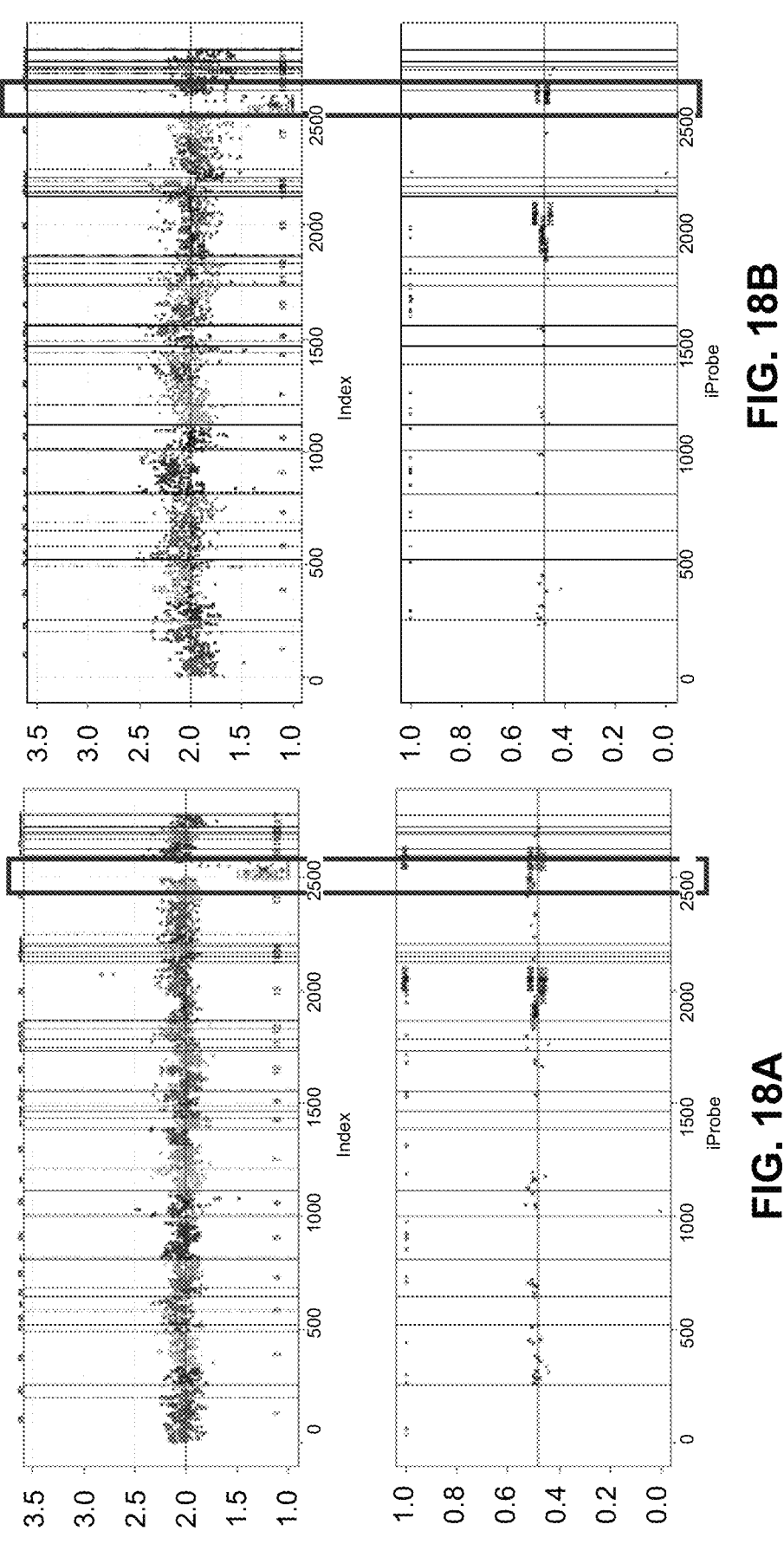
FIG. 18A illustrates an example plot of BRCA1 homozygous deletions, according to an embodiment of the disclosure.
FIG. 18B illustrates an example plot of BRCA1 homozygous deletions, according to an embodiment of the disclosure.
Figures 19A, 19B:
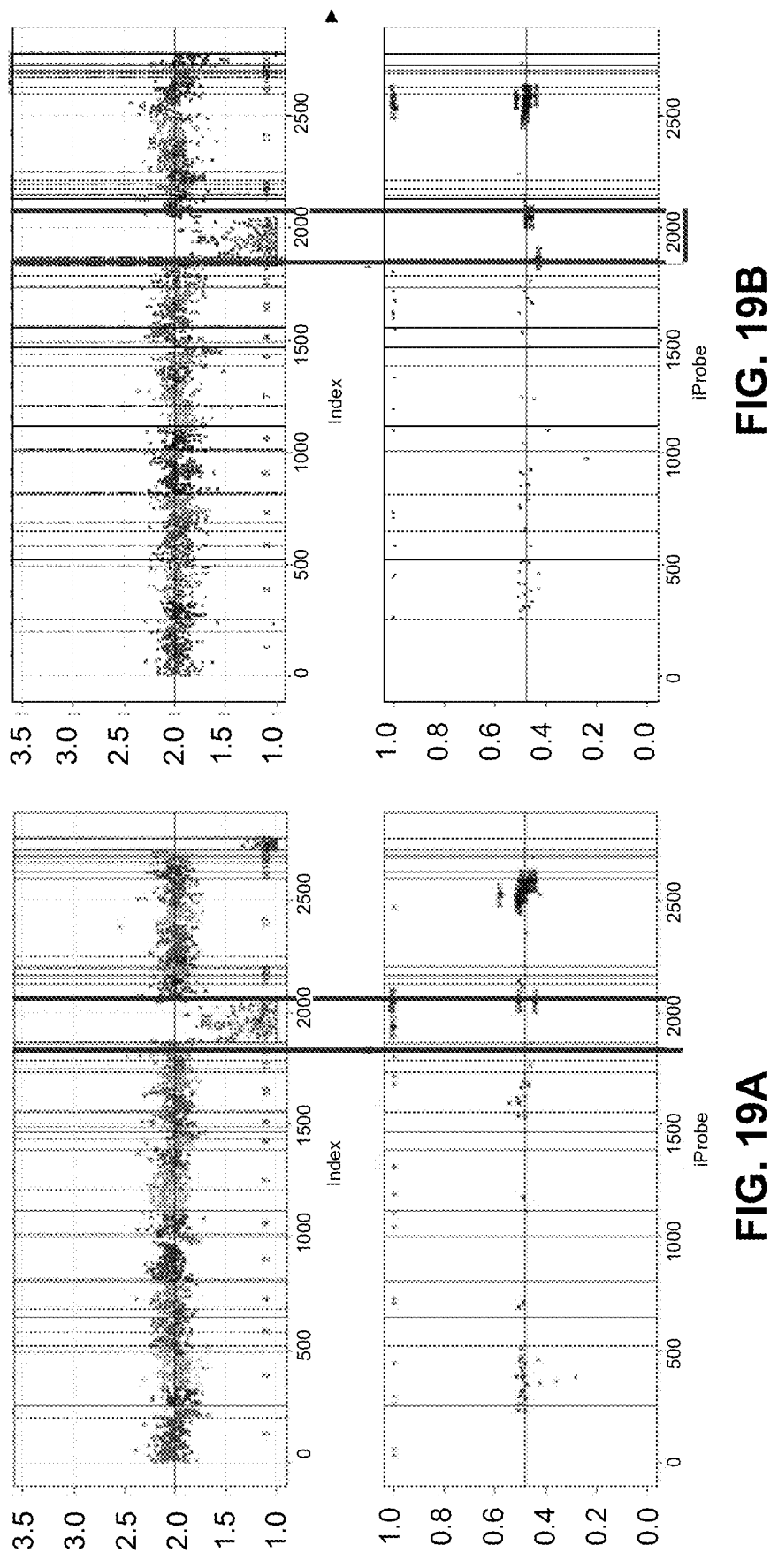
FIG. 19A illustrates an example plot of BRCA2 homozygous deletions, according to an embodiment of the disclosure.
FIG. 19B illustrates an example plot of BRCA2 homozygous deletions, according to an embodiment of the disclosure.

FIG. 18A illustrates an example plot of BRCA1 homozygous deletions, according to an embodiment of the disclosure. FIG. 18B illustrates an example plot of BRCA1 homozygous deletions, according to an embodiment of the disclosure. FIG. 19A illustrates an example plot of BRCA2 homozygous deletions, according to an embodiment of the disclosure. FIG. 19B illustrates an example plot of BRCA2 homozygous deletions, according to an embodiment of the disclosure. FIGS. 18A, 18B, 19A, and 19B are plots based on the human genome.

Figures 20A, 20B:
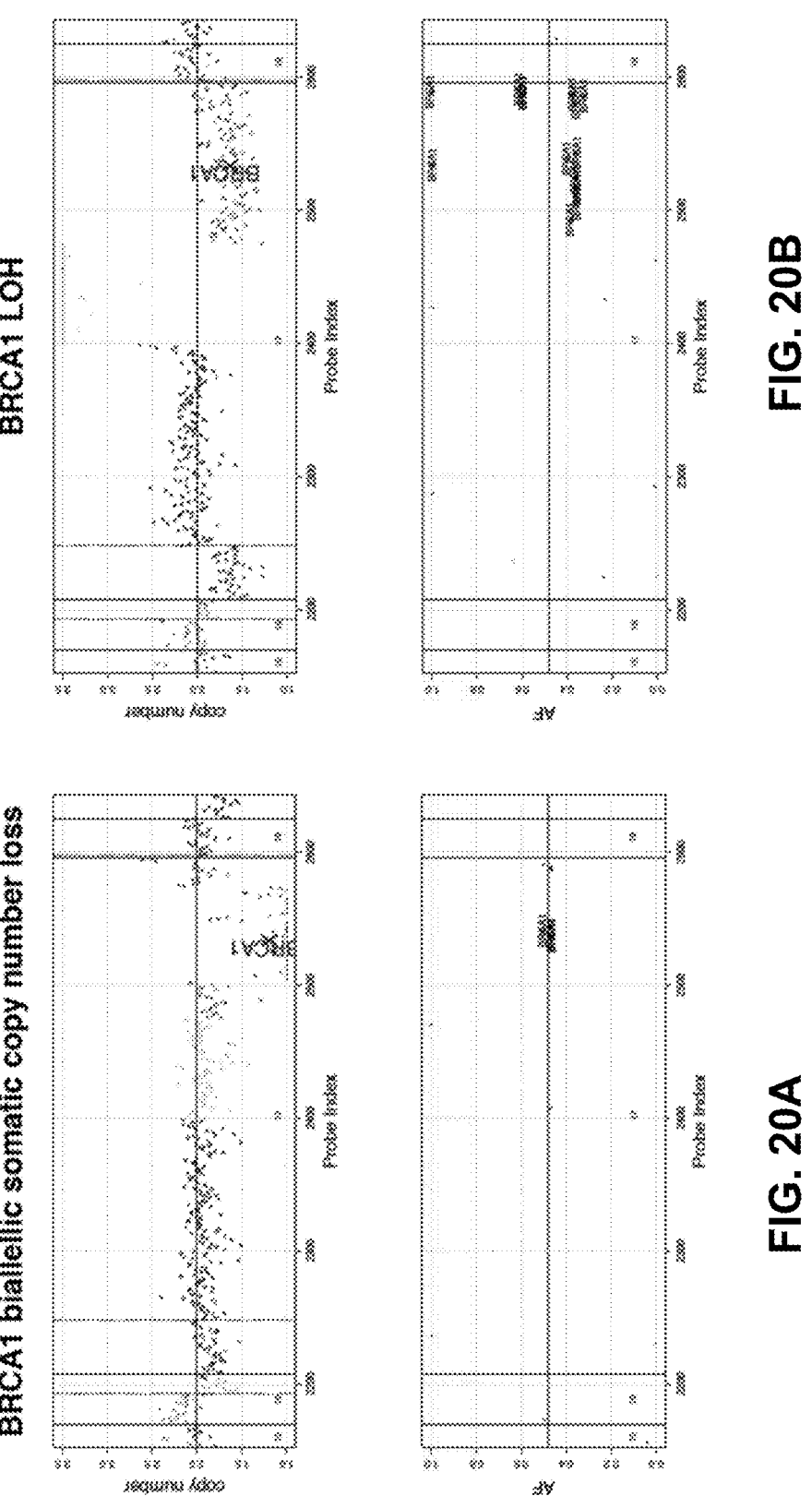
FIG. 20A illustrates an example plot of BRCA1 biallelic somatic copy number loss, according to an embodiment of the disclosure.
FIG. 20B illustrates an example plot of BRCA1 LOH, according to an embodiment of the disclosure.
Figures 21A, 21B:
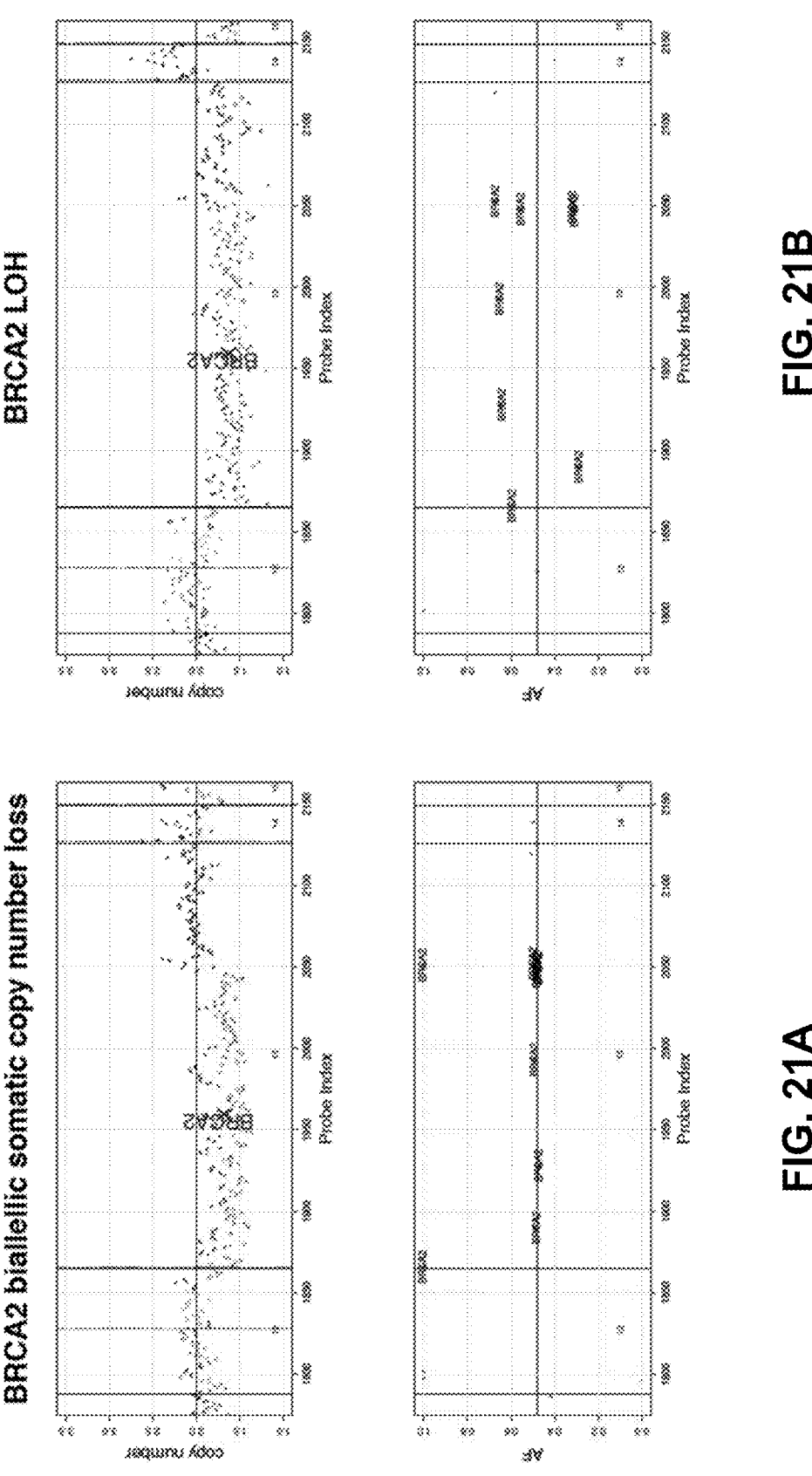
FIG. 21A illustrates an example plot of BRCA2 biallelic somatic copy number loss, according to an embodiment of the disclosure.
FIG. 21B illustrates an example plot of BRCA2 LOH, according to an embodiment of the disclosure.
Figure 22:
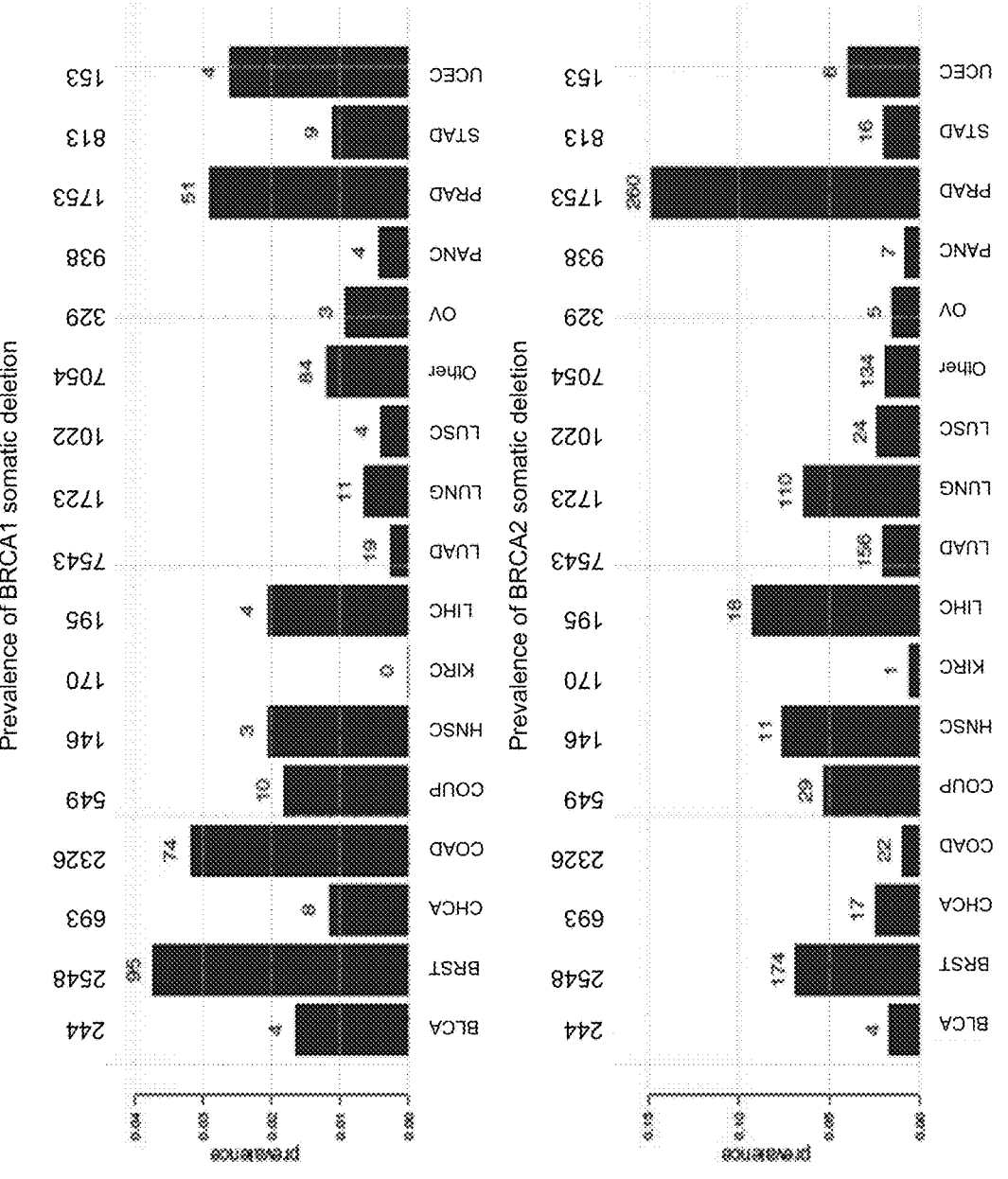
FIG. 22 illustrates a plot of the prevalence of BRCA1 and BRCA2 somatic deletions, according to an embodiment of the disclosure.

FIG. 20A illustrates an example plot of BRCA1 biallelic somatic copy number loss, according to an embodiment of the disclosure. For purposes of this disclosure, the term "biallelic somatic copy number loss" will be used interchangeably with "homozygous deletion." FIG. 20B illustrates an example plot of BRCA1 LOH, according to an embodiment of the disclosure. For purposes of this disclosure, the term "LOH" will be used interchangeably with "heterozygous deletion." FIG. 21A illustrates an example plot of BRCA2 biallelic somatic copy number loss, according to an embodiment of the disclosure. FIG. 21B illustrates an example plot of BRCA2 LOH, according to an embodiment of the disclosure. FIGS. 20A, 20B, 21A, and 21B are plots based on three (human) chromosomes. FIG. 22 illustrates a plot of the prevalence of BRCA1 and BRCA2 somatic deletions, according to an embodiment of the disclosure.

Computer Implementation

The present methods can be computer-implemented, such that any or all of the steps described in the specification or appended claims other than wet chemistry steps can be performed in a suitable programmed computer. The computer can be a mainframe, personal computer, tablet, smart phone, cloud, online data storage, remote data storage, or the like. The computer can be operated in one or more locations.

Various operations of the present methods can utilize information and/or programs and generate results that are stored on computer-readable media (e.g., hard drive, auxiliary memory, external memory, server; database, portable memory device (e.g., CD-R, DVD, ZIP disk, flash memory cards), and the like.

The present disclosure also includes an article of manufacture for analyzing a nucleic acid population that includes a machine-readable medium containing one or more programs which when executed implement the steps of the present methods.

The disclosure can be implemented in hardware and/or software. For example, different aspects of the disclosure can be implemented in either client-side logic or server-side logic. The disclosure or components thereof can be embodied in a fixed media program component containing logic instructions and/or data that when loaded into an appropriately configured computing device cause that device to perform according to the disclosure. A fixed media containing logic instructions can be delivered to a viewer on a fixed media for physically loading into a viewer's computer or a fixed media containing logic instructions may reside on a remote server that a viewer accesses through a communication medium to download a program component.

The present disclosure provides computer control systems that are programmed to implement methods of the disclosure. The processor 120 may include a single core or multi core processor, or a plurality of processors for parallel processing. The storage device 122 may include random-access memory, read-only memory, flash memory, a hard disk, and/or other type of storage. The computer system 110 may include a communication interface (e.g., network adapter) for communicating with one or more other systems, and peripheral devices, such as cache, other memory, data storage and/or electronic display adapters. The components of the computer system 110 may communicate with one another through an internal communication bus, such as a motherboard. The storage device 122 may be a data storage unit (or data repository) for storing data. The computer system 110 may be operatively coupled to a computer network ("network") with the aid of the communication interface. The network may be the Internet, an internet and/or extranet, or an intranet and/or extranet that is in communication with the Internet. The network in some cases is a telecommunication and/or data network. The network may include a local area network. The network may include one or more computer servers, which can enable distributed computing, such as cloud computing. The network, in some cases with the aid of the computer system 110, may implement a peer-to-peer network, which may enable devices coupled to the computer system 120 to behave as a client or a server.

The processor 120 may execute a sequence of machine-readable instructions, which can be embodied in a program or software. The instructions may be stored in a memory location, such as the storage device 122. The instructions can be directed to the processor 120, which can subsequently program or otherwise configure the processor 120 to implement methods of the present disclosure. Examples of operations performed by the processor 120 may include fetch, decode, execute, and writeback.

The processor 120 may be part of a circuit, such as an integrated circuit. One or more other components of the system 100 may be included in the circuit. In some cases, the circuit may include an application specific integrated circuit (ASIC).

The storage device 122 may store files, such as drivers, libraries and saved programs. The storage device 122 can store user data, e.g., user preferences and user programs. The computer system 110 in some cases may include one or more additional data storage units that are external to the computer system 110, such as located on a remote server that is in communication with the computer system 110 through an intranet or the Internet.

The computer system 110 can communicate with one or more remote computer systems through the network. For instance, the computer system 110 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 110 via the network.

Methods as described herein can be implemented by way of machine (e.g., computer processor) executable code stored on an electronic storage location of the computer system 110, such as, for example, on the storage device 122. The machine executable or machine readable code can be provided in the form of software. During use, the code can be executed by the processor 905. In some cases, the code can be retrieved from the storage unit 915 and stored on the storage device 122 for ready access by the processor 120.

The code may be pre-compiled and configured for use with a machine having a processer adapted to execute the code, or can be compiled during runtime. The code can be supplied in a programming language that can be selected to enable the code to execute in a precompiled or as-compiled fashion.

Aspects of the systems and methods provided herein, such as the computer system 110, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk.

"Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "Storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 110 can include or be in communication with an electronic display 935 that comprises a user interface (UI) for providing, for example, a report. Examples of UI's include, without limitation, a graphical user interface (GUI) and web-based user interface.

Methods and systems of the present disclosure can be implemented by way of one or more algorithms. An algorithm can be implemented by way of software upon execution by the processor 120.

Sample Collection and Analysis Pipeline

A sample 101 may be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. Such samples may include nucleic acids. Such samples may be referred to as nucleic acid samples. In some of these samples, the nucleic acids may be shed from tumors. The nucleic acids can include DNA and RNA and can be in double- and/or single-stranded forms. In examples in which the nucleic acids include RNA, the systems and methods described herein may determine a somatic deletion in a gene of interest encoded by the RNA by comparing the gene expression of the gene of interest relative to a reference gene (such as an endogenous control gene like GAPDH) to a trained threshold value calculated from normal samples. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid for analysis is plasma or serum containing cell-free nucleic acids, e.g., cell-free DNA (cfDNA).

The volume of plasma can depend on the desired read depth for sequenced regions. Exemplary volumes are 0.4-40 ml, 5-20 ml, 10-20 ml. For example, the volume can be 0.5 ml, 1 ml, 5 ml, 10 ml, 20 ml, 30 ml, or 40 ml. A volume of sampled plasma may be 5 to 20 ml.

The sample can comprise various amounts of nucleic acid that contains genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., from cells and cell free. A sample can comprise nucleic acids carrying mutations. For example, a sample can comprise DNA carrying germline mutations and/or somatic mutations. A sample can comprise DNA carrying cancer-associated mutations (e.g., cancer-associated somatic mutations).

Exemplary amounts of cell free nucleic acids in a sample before amplification range from about 1 fg to about 1 µg, e.g., 1 pg to 200 ng, 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng.

A cell-free nucleic acid sample refers to a sample from a subject containing cell-free nucleic acids. Cell-free nucleic acids are nucleic acids not contained within or otherwise bound to a cell. For example, a cell-free nucleic acid sample may include nucleic acids remaining in the sample after removing intact cells. Cell-free nucleic acids can be referred to all non-encapsulated nucleic acid sourced from a bodily fluid (e.g., blood, urine, CSF, etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or a hybrid thereof. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA (ctDNA). Others are released from healthy cells. ctDNA can be non-encapsulated tumor-derived fragmented DNA. Cell-free fetal DNA (cffDNA) is fetal DNA circulating freely in the maternal blood stream.

A cell-free nucleic acid or proteins associated with it can have one or more epigenetic modifications, for example, a cell-free nucleic acid can be acetylated, 5-methylated, ubiquitylated, phosphorylated, sumoylated, ribosylated, and/or citrullinated.

Cell-free nucleic acids have an exemplary size distribution of about 100-500 nucleotides, with molecules of 110 to about 230 nucleotides representing about 90% of molecules, with a mode of about 168 nucleotides in humans and a second minor peak in a range between 240 to 440 nucleotides. Cell-free nucleic acids can be about 160 to about 180 nucleotides, or about 320 to about 360 nucleotides, or about 440 to about 480 nucleotides.

Cell-free nucleic acids can be isolated from bodily fluids through a partitioning step in which cell-free nucleic acids, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, cell-free nucleic acids can be precipitated with an alcohol. Further clean up steps may be used such as silica based columns to remove contaminants or salts. Non-specific bulk carrier nucleic acids, for example, may be added throughout the reaction to optimize certain aspects of the procedure such as yield.

After such processing, samples can include various forms of nucleic acid including double-stranded DNA, single stranded DNA and single stranded RNA. Optionally, single stranded DNA and RNA can be converted to double-stranded forms so they are included in subsequent processing and analysis steps.

Tags

In some embodiments, the nucleic acid molecules (from the sample of polynucleotides) may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located at one end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-uniquely tagged molecular barcodes in combination with endogenous sequence information (e.g., the beginning (start) and/or end (stop) portions corresponding to the sequence of the original nucleic acid molecule in the sample, sub-sequences of sequence reads at one or both ends, length of sequence reads, and/or length of the original nucleic acid molecule in the sample) typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of identifiers (e.g., a combination of unique or non-unique molecular barcodes) to molecules in a sample. One example format uses from about 2 to about 1,000,000 different molecular barcodes, or from about 5 to about 150 different molecular barcodes, or from about 20 to about 50 different molecular barcodes, ligated to both ends of a target molecule. Alternatively, from about 25 to about 1,000,000 different molecular barcodes may be used. For example, 20-50×20-50 molecular barcodes can be used. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. Patent Application Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

Amplification

Sample nucleic acids flanked by adapters can be amplified by PCR and other amplification methods typically primed from primers binding to primer binding sites in adapters flanking a DNA molecule to be amplified. Amplification methods can involve cycles of extension, denaturation and annealing resulting from thermocycling or can be isothermal as in transcription mediated amplification. Other amplification methods include the ligase chain reaction, strand displacement amplification, nucleic acid sequence based amplification, and self-sustained sequence based replication.

One or more amplifications can be applied to introduce barcodes to a nucleic acid molecule using conventional nucleic acid amplification methods. The amplification can be conducted in one or more reaction mixtures. Molecule tags and sample indexes/tags can be introduced simultaneously, or in any sequential order. Molecule tags and sample indexes/tags can be introduced prior to and/or after sequence capturing. In some cases, only the molecule tags are introduced prior to probe capturing while the sample indexes/tags are introduced after sequence capturing. In some cases, both the molecule tags and the sample indexes/tags are introduced prior to probe capturing. In some cases, the sample indexes/tags are introduced after sequence capturing. Usually, sequence capturing involves introducing a single-stranded nucleic acid molecule complementary to a targeted sequence, e.g., a coding sequence of a genomic region and mutation of such region is associated with a cancer type. Typically, the amplifications generate a plurality of non-uniquely or uniquely tagged nucleic acid amplicons with molecule tags and sample indexes/tags at a size ranging from 200 nt to 700 nt, 250 nt to 350 nt, or 320 nt to 550 nt.

In some embodiments, the amplicons have a size of about 300 nt. In some embodiments, the amplicons have a size of about 500 nt.

Enrichment

In some embodiments, sequences are enriched prior to sequencing the nucleic acids. Enrichment is optionally performed for specific target regions or nonspecifically ("target sequences"). In some embodiments, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest.

Sequence capture typically involves the use of oligonucleotide probes that hybridize to the target nucleic acid sequence. In certain embodiments, a probe set strategy involves tiling the probes across a region of interest. Such probes can be, for example, from about 60 to about 120 nucleotides in length. The set can have a depth of about 2x, 3x, 4x, 5x, 6x, 8x, 9x, 10x, 15x, 20x, 50x or more. The effectiveness of sequence capture generally depends, in part, on the length of the sequence in the target molecule that is complementary (or nearly complementary) to the sequence of the probe. In some embodiments, the enriched population may be amplified prior to sequencing.

Sequencing Pipeline

Sample nucleic acids flanked by adapters with or without prior amplification can be subject to sequencing, such as by one or more sequencing devices 107. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may be multiple lanes, multiple channels, multiple wells, or other means of processing multiple sample sets substantially simultaneously. Sample processing unit can also include multiple sample chambers to enable processing of multiple runs simultaneously.

The sequencing reactions can be performed on one or more fragments types known to contain markers of cancer of other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9% or 100%. In other cases, sequence coverage of the genome may be less than 5%, 10%, 15%, 20%, 25%, 30%, 40%, 50%, 60%, 70%, 80%, 90%, 95%, 99%, 99.9% or 100%.

Simultaneous sequencing reactions may be performed using multiplex sequencing. In some cases, cell free polynucleotides may be sequenced with at least 1000, 2000, 3000, 4000, 5000, 6000, 7000, 8000, 9000, 10000, 50000, 100,000 sequencing reactions. In other cases, cell free polynucleotides may be sequenced with less than 1000, 2000, 3000, 4000, 5000, 6000, 7000, 8000, 9000, 10000, 50000, 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, 100,000 sequencing reactions. In other cases, data analysis may be performed on less than 1000, 2000, 3000, 4000, 5000, 6000, 7000, 8000, 9000, 10000, 50000, 100,000 sequencing reactions. An exemplary read depth is 1000-80000 reads per locus (base).

Sequence Analysis Pipeline

In some embodiments, nucleic acids in the sample may be contacted with a sufficient number of adapters comprising molecular barcodes such that there is a low probability (e.g., <1 or 0.1%) that any two copies of the same nucleic acid molecule receive the same combination of molecular barcodes from the adapters linked at both ends. The use of adapters in this manner permits identification of families of nucleic acid sequences (sequence reads) that are generated from a given nucleic acid molecule. For example, nucleic acid sequences having the same start and stop points on a reference sequence and linked to the same combination of molecular barcodes may be deemed to be part of a family. As such, a family represents sequences of amplification products of a given nucleic acid molecule in the sample, in which a family member is a sequence read generated from an amplification product. The sequences of family members can be compiled to derive consensus nucleotide(s) or a complete consensus sequence for a nucleic acid molecule in the original sample, as modified by blunt end formation and adapter attachment. In other words, the nucleotide occupying a specified position of a nucleic acid in the sample is determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 9, or 10 sequenced nucleic acids within the subset including the nucleotide variant or it can be a ratio, such as a least 0.5, 1, 2, 3, 4, 5, 10, 15, or 20 of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

The present methods can be used to identify presence or absence of genetic events that may cause conditions, particularly cancer, in a subject, to characterize conditions (e.g., staging cancer or determining heterogeneity of a cancer), monitor response to treatment of a condition, effect prognosis risk of developing a condition or subsequent course of a condition.

Various cancers may be detected using the present methods. Cancer cells, as most cells, can be characterized by a rate of turnover, in which old cells die and replaced by newer cells. Generally dead cells, in contact with vasculature in a given subject, may release DNA or fragments of DNA into the blood stream. This is also true of cancer cells during various stages of the disease. Cancer cells may also be characterized, dependent on the stage of the disease, by various genetic aberrations such as copy number variation as well as rare mutations. This phenomenon may be used to detect the presence or absence of cancers in individuals using the methods and systems described herein.

The types and number of cancers that may be detected may include blood cancers, brain cancers, lung cancers, skin cancers, nose cancers, throat cancers, liver cancers, bone cancers, lymphomas, pancreatic cancers, skin cancers, bowel cancers, rectal cancers, thyroid cancers, bladder cancers, kidney cancers, mouth cancers, stomach cancers, solid state tumors, heterogeneous tumors, homogenous tumors and the like.

Cancers can be detected from genetic variations including mutations, rare mutations, indels, copy number variations, transversions, translocations, inversion, deletions, aneuploidy, partial aneuploidy, polyploidy, chromosomal instability, chromosomal structure alterations, gene fusions, chromosome fusions, gene truncations, gene amplification, gene duplications, chromosomal lesions, DNA lesions, abnormal changes in nucleic acid chemical modifications, abnormal changes in epigenetic patterns.

Genetic data can also be used for characterizing a specific form of cancer. Cancers are often heterogeneous in both composition and staging. Genetic profile data may allow characterization of specific sub-types of cancer that may be important in the diagnosis or treatment of that specific sub-type. This information may also provide a subject or practitioner clues regarding the prognosis of a specific type of cancer and allow either a subject or practitioner to adapt treatment options in accord with the progress of the disease. Some cancers progress, becoming more aggressive and genetically unstable. Other cancers may remain benign, inactive or dormant. The system and methods of this disclosure may be useful in determining disease progression.

The present analysis is also useful in determining the efficacy of a particular treatment option. Successful treatment options may increase the amount of copy number variation or rare mutations detected in a subject's blood if the treatment is successful as more cancers may die and shed DNA. In other examples, this may not occur. In another example, perhaps certain treatment options may be correlated with genetic profiles of cancers over time. This correlation may be useful in selecting a therapy. Additionally, if a cancer is observed to be in remission after treatment, the present methods can be used to monitor residual disease or recurrence of disease.

The present methods can also be used for detecting genetic variations in conditions other than cancer. Immune cells, such as B cells, may undergo rapid clonal expansion upon the presence certain diseases. Clonal expansions may be monitored using copy number variation detection and certain immune states may be monitored. In this example, copy number variation analysis may be performed over time to produce a profile of how a particular disease may be progressing. Copy number variation or even rare mutation detection may be used to determine how a population of pathogens are changing during the course of infection. This may be particularly important during chronic infections, such as HIV/AIDs or Hepatitis infections, whereby viruses may change life cycle state and/or mutate into more virulent forms during the course of infection. The present methods may be used to determine or profile rejection activities of the host body, as immune cells attempt to destroy transplanted tissue to monitor the status of transplanted tissue as well as altering the course of treatment or prevention of rejection.

Further, the methods of the disclosure may be used to characterize the heterogeneity of an abnormal condition in a subject, the method comprising generating a genetic profile of extracellular polynucleotides in the subject, wherein the genetic profile comprises a plurality of data resulting from copy number variation and rare mutation analyses. In some cases, including but not limited to cancer, a disease may be heterogeneous. Disease cells may not be identical. In the example of cancer, some tumors are known to comprise different types of tumor cells, some cells in different stages of the cancer. In other examples, heterogeneity may comprise multiple foci of disease. Again, in the example of cancer, there may be multiple tumor foci, perhaps where one or more foci are the result of metastases that have spread from a primary site.

The present methods can be used to generate or profile, fingerprint or set of data that is a summation of genetic information derived from different cells in a heterogeneous disease. This set of data may comprise copy number variation and rare mutation analyses alone or in combination.

The present methods can be used to diagnose, prognose, monitor or observe cancers or other diseases of fetal origin. That is, these methodologies may be employed in a pregnant subject to diagnose, prognose, monitor or observe cancers or other diseases in an unborn subject whose DNA and other polynucleotides may co-circulate with maternal molecules.

Precision Treatment Examples

The precision diagnostics provided by the improved computer system 110 may result in precision treatment plans, which may be identified by the computer system 110 (and/or curated by health professionals). For example, one type of precision diagnostic and treatment may relate to genes in the homologous recombination repair (HRR) pathway.

Homologous recombination is a type of genetic recombination in which nucleotide sequences are exchanged between two similar or identical molecules of DNA. It is most widely used by cells to accurately repair harmful breaks that occur on both strands of DNA, known as double-strand breaks (DSB). HRR provides a mechanism for the error-free removal of damage present in DNA that has replicated (S and G2 phases), to eliminate chromosomal breaks before the cell division occurs. The primary model for how homologous recombination repairs double-strand breaks in DNA is homologous recombination repair pathway which mediates the double-strand break repair (DSBR) pathway and the synthesis-dependent strand annealing (SDSA) pathway. Germline and somatic deficiencies in homologous recombination genes have been strongly linked to breast, ovarian and prostate cancers.

The number and types of variant nucleotides in a sample can provide an indication of the amenability of the subject providing the sample to treatment, i.e., therapeutic intervention. For example, various poly ADP ribose polymerase (PARP) inhibitors have been shown to stop the growth of tumors from breast, ovarian and prostate cancers caused by hereditary mutations in the BRCA1 or BRCA2 genes. Some of these therapeutic agents may inhibit base excision repair (BER), which may compensate for the deficiency of HRR.

On the other hand, certain BRCA and HRR wildtype patients may not achieve clinical benefit from treatment with a PARP inhibitor. Furthermore, not all ovarian cancer patients with a BRCA mutation will respond to a PARP inhibitor. Moreover, different types of mutations may indicate different therapies. For example, somatic heterozygous deletions in HRR genes may indicate a different therapy than somatic homozygous deletions. Thus, the state of genetic material may influence therapy. In one example, a PARP inhibitor may be administered to an individual harboring a somatic homozygous deletion in an HRR gene, but not to an individual harboring a wildtype allele or somatic heterozygous deletions in the HRR gene.

Nucleotide variations in sequenced nucleic acids can be determined by comparing sequenced nucleic acids with a reference sequence. The reference sequence is often a known sequence, e.g., a known whole or partial genome sequence from an object, whole genome sequence of a human object. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acid within the subset including the nucleotide variant or it can be a ratio, such a least 0.5, 1, 2, 3, 4, 5, 10, 15, or 20 of sequenced nucleic acids within the subset include the nucleotide variant, among other possibilities. The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions.

EXAMPLES

The modeling described herein was applied to plasma samples from 28,199 patients with advanced solid tumors sequenced using a 73-gene next generation sequencing ctDNA panel from Guardant Health, Inc.

Examples of results showed 95% sensitivity in detecting BRCA1/2 gene deletions for samples showing a tumor fraction of 9%-11%. Limit of detection for LOH and biallelic copy number loss is 11%-13%. The observed prevalence of BRCA1 somatic deletions is higher than 3% in breast, colorectal, prostate and endometrial cancers. The observed prevalence of BRCA2 somatic deletions is higher than 6% in breast, lung, prostate, head and neck (HNSCC) and hepatocellular carcinoma.

In a cohort of 5,568 patients with classic HRD associated cancers, somatic LOH and biallelic somatic copy number loss was detected in BRCA1 in 2.7% of samples and in BRCA2 in 8.0% of samples, which is aligned with previously reported tissue prevalence. BRCA1 and BRCA2 LOH was observed in 2.4% (134/5568) and 7.4% (415/5568) of classic homologous recombination deficient (HRD) cancers including breast, ovarian, prostate, and pancreas. BRCA1 and BRCA2 biallelic somatic copy number loss was observed in 0.3% (19/5568) and 0.5% (31/5568) of this same group of HRD cancers. BRCA1/2 somatic LOH and biallelic somatic copy number loss may be accurately detected in ctDNA based on application of the models described herein. The ability to identify this therapeutically targetable genomic alteration through a non-invasive ctDNA assessment has significant clinical implications, especially in patients whose disease challenges tissue testing because of deep visceral location, predominantly bone and brain metastasis such as breast and prostate cancers.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A system to distinguish between a somatic homozygous deletion and a somatic heterozygous deletion of a gene in a sample of cell-free nucleic acid molecules that does not exhibit germline deletion of the gene, the system comprising:

a sequencing system configured to receive and process the sample of cell-free nucleic acid molecules collected from a subject, the sequencing system comprising:

a sequencing pipeline having one or more sequencing devices for associating cell-free nucleic acid molecules of the sample collected from the subject with sequence reads;

a processor programmed to:

receive, via a sequence analysis pipeline, sequence reads from the sequencing system;

receive, via a pre-processing subsystem, data from the sequence analysis pipeline;

generate, via the pre-processing subsystem, training datasets;

store the training datasets in a training datastore;

based on the training datasets, implement a classifier to generate, via a first probabilistic distribution, a first model of allelic counts based on one or more germline heterozygous single nucleotide polymorphism (SNP) positions associated with the gene in the sample, the first model representing the somatic homozygous deletion;

based on the training datasets, implement the classifier to generate, via a second probabilistic distribution, a second model of allelic counts in the sample based on the one or more germline heterozygous SNP positions, the second model representing the somatic heterozygous deletion;

implement the classifier to compare a first output of the first model and a second output of the second model;

implement the classifier to generate a prediction that the somatic homozygous deletion for the gene exists in the sample of cell-free nucleic acid molecules based on the comparison, thereby improving the accuracy of detecting the somatic homozygous deletion in the sample of cell-free nucleic acid molecules, wherein detecting the existence of the somatic homozygous deletion in the sample of cell-free nucleic acid molecules indicates the subject as one who has homologous repair deficiency (HRD) and may benefit from an anti-cancer therapy; and generating a precision treatment plan tailored to the subject based on the prediction that the somatic homozygous deletion for the genes exists in the sample of cell-free nucleic acid molecules, wherein the precision treatment plan comprises administering a poly ADP ribose polymerase (PARP) inhibitor to the subject.

2. The system of claim 1, wherein the first model represents a first probability that the sample includes the somatic homozygous deletion and the second model represents a second probability that the sample includes the somatic heterozygous deletion.

3. The system of claim 1, wherein the first probabilistic distribution is a same type of probabilistic distribution as the second probabilistic distribution.

4. The system of claim 1, wherein to generate the first model, the processor is programmed to determine one or more parameters for input to the first probabilistic distribution.

5. The system of claim 4, wherein the first probabilistic distribution comprises a type of probabilistic distribution comprising one of: a beta-binomial distribution, a binomial distribution, or a normal distribution.

6. The system of claim 4, wherein to generate the first model of allelic counts, the processor is further programmed to:

determine, for input to the first probabilistic distribution, a prevalence of heterozygosity of the one or more germline SNPs in a training set of samples.

7. The system of claim 6, wherein the training set of samples comprises a plurality of samples in which tumor is not detected (TND).

8. The system of claim 6, wherein to generate the first model of allelic counts, the processor is further programmed to:

determine, for input to the first probabilistic distribution, a standard deviation of a minor allele frequency (MAF) associated with the one or more germline SNPs in the training set of samples.

9. The system of claim 8, wherein to generate the first model, the processor is further programmed to:

determine, for input to the first probabilistic distribution, a number of molecules in the sample that supports a mutant allele.

10. The system of claim 9, wherein to generate the first model, the processor is further programmed to:

determine, for input to the first probabilistic distribution, a total number of molecules in the sample.

11. The system of claim 10, wherein to generate the first model, the processor is further programmed to:

calculate a first likelihood of the allelic counts of the one or more germline SNP positions in the sample assuming somatic homozygous deletion based on molecule coverage associated with the somatic homozygous deletion.

12. The system of claim 11, wherein to generate the second model, the processor is further programmed to:

calculate a second likelihood of the allelic counts of the one or more germline SNP positions in the sample assuming somatic heterozygous deletion based on molecule coverage associated with the somatic heterozygous deletion.

13. The system of claim 4, wherein to generate the second model, the processor is further programmed to:

determine, for input to the second probabilistic distribution for the second model, a mean of tumor fraction estimated from the sample.

14. The system of claim 13, wherein the tumor fraction is estimated based on sequence coverage information.

15. The system of claim 13, wherein to generate the second model, the processor is further programmed to:

determine, for input to the second probabilistic distribution for the second model, a standard deviation of tumor fraction estimated from the sample.

16. The system of claim 1, wherein the processor is further programmed to:

access a plurality of samples;

identify a set of samples from among the plurality of samples that include a germline deletion;

filter out the set of samples from the plurality of samples; and identify, from among the filtered plurality of samples, a presence of the somatic homozygous deletion or the somatic heterozygous deletion.

17. The system of claim 1, wherein the first output comprises a first probability of a presence of the somatic homozygous deletion and the second output comprises a second probability of a presence of the somatic heterozygous deletion.

18. The system of claim 1, wherein to compare the first output of the first model and the second output of the second model, the processor is further programmed to:

execute a log likelihood function based on the first output and the second output.

19. The system of claim 1, wherein the gene comprises one of: BRCA1, BRCA2, and ATM.

\* \* \* \* \*